US 7,709,190 B2

(12) United States Patent
Montelione et al.

(10) Patent No.: US 7,709,190 B2
(45) Date of Patent: *May 4, 2010

(54) INFLUENZA A VIRUS VACCINES AND INHIBITORS

(75) Inventors: Gaetano Montelione, Highland Park, NJ (US); Kalyan Das, Edison, NJ (US); Edward Arnold, Belle Mead, NJ (US); LiChung Ma, Plainsboro, NJ (US); Rong Xiao, Princeton, NJ (US); Robert M. Krug, Austin, TX (US); Karen Y. Twu, Austin, TX (US); Rei-Lin Kuo, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 373 days.

This patent is subject to a terminal disclaimer.

(21) Appl. No.: 11/566,216

(22) Filed: Dec. 2, 2006

(65) Prior Publication Data

US 2008/0108050 A1    May 8, 2008

Related U.S. Application Data

(60) Provisional application No. 60/741,764, filed on Dec. 2, 2005, provisional application No. 60/852,361, filed on Oct. 16, 2006.

(51) Int. Cl.
*C12Q 1/70*    (2006.01)
(52) U.S. Cl. .......................................................... 435/5

(58) Field of Classification Search ...................... None
See application file for complete search history.

(56) References Cited

U.S. PATENT DOCUMENTS 6,593,091 B2    7/2003   Keys et al.

FOREIGN PATENT DOCUMENTS

WO    2004/043404 A2    9/2004
WO    2007/061969 A2    5/2007

OTHER PUBLICATIONS

Greenspan, et al. Two Nuclear Location Signals in the Influenza Virus NS1 Nonstructural Protein. J Virol.1988; 62(8): 3020-3026.*
Salvatore and Garcia-Sastre (2001).*

(Continued)

*Primary Examiner*—Mary E Mosher
*Assistant Examiner*—Stuart W Snyder
(74) *Attorney, Agent, or Firm*—Edwin S. Flores; Chainey P. Singleton; Chalker Flores, LLP

(57)    ABSTRACT

The present invention includes compositions and methods related to the structure and function of the cellular polyadenylation and specificity factor 30 (CPSF30) binding site on the surface of the influenza A non-structural protein 1 (NS1). Specifically, critical biochemical reagents, conditions for crystallization and NMR analysis, assays, and general processes are described for (i) discovering, designing, and optimizing small molecule inhibitors of influenza A (avian flu) viruses and (ii) creating attenuated influenza virus strains suitable for avian and human flu vaccine development.

29 Claims, 5 Drawing Sheets

OTHER PUBLICATIONS

Rice, et al. Inhibitors of HIV nucleocapsid protein zinc fingers as candidates for the treatment of AIDS. Science; Nov. 17, 1995; 270, 5239: 1194-7.*

Elton, et al. Identification of Amino Acid Residues of Influenza Virus Nucleoprotein Essential for RNA Binding. Journal of Virology. 1999; vol. 73, No. 9:7357-7367.*

Kim, M.J., et al., "Human influenza viruses activate an interferon-independent transcription of celluar antiviral genes: outcome with influenza A virus is unique." Proc Natl Acad Sci U S A (2002), 99:10096-101.

Krug, R.M., et al., "Intracellular warfare between human influenza viruses and human cells: the roles of the viral NS1 protein." Virology (2003), 309:181-9.

Li, Y., et al., "The 3'-end-processing factor CPSF is required for the splicing of single-intron pre-mRNAs in vivo." RNA (2001), 7:920-31.

Nemeroff, M., et al., "Influenza virus NS1 protein interacts with the 30 kD subunit of cleavage and specificity factor and inhibits 3' end formation of cellular pre-mRNAs." Mol. Cell (1998), 1:991-1000.

Noah, D.L., et al., "Cellular antiviral responses against influenza A virus are countered at the posttranscriptional level by the viral NS1A protein via its binding to a cellular protein required for the 3' end processing of cellular pre-mRNAS." Virology (2003), 307:386-95.

Twu, K.Y., et al., "The CPSF30 binding site on the NS1A protein of influenza A virus is a potential antiviral target." J Virol (2006), 80:3957-65.

Salvatore, M., et al., "Virus versus host: modulation of the host a/β interferon pathways by the influenza A virus NS1 protein," International Congress Series (2001), 1219:513-520.

International Search Report and Written Opinion for PCT/US2006/046239 dated May 2, 2008.

Ohnishi, H., et al., "Mechanism of Host Defense Suppression Induced by Viral Infection: Mode of Action of Inosiplex as an Antiviral Agent," Infection and Immunity (1982), 38:243-250.

Yoneyama, M., et al., "Direct Triggering of the Type I Interferon System by Virus Infection: Activation of a Transcription Factor Complex containing IRF-3 and CBP/p300," EMBO Journal (1998), 17:1087-1095.

* cited by examiner

INFLUENZA A VIRUS VACCINES AND INHIBITORS

CROSS-REFERENCE TO RELATED APPLICATIONS

This application claims priority to U.S. Provisional Application Ser. No. 60/741,764, filed Dec. 2, 2005 and Ser. No. 60/852,361 filed Oct. 16, 2006, the entire contents of which are incorporated herein by reference. This application is related to U.S. patent application Ser. No. 11/566,214, filed on Dec. 2, 2006.

STATEMENT OF FEDERALLY FUNDED RESEARCH

This invention was made with U.S. Government support under Contract Nos. AI-11772 awarded by the NIH. The government has certain rights in this invention.

TECHNICAL FIELD OF THE INVENTION

The present invention relates in general to the field of anti-viral assays and molecules, and more particularly, to compositions and methods for developing, isolating and characterizing novel Influenza A virus inhibitors and vaccines.

INCORPORATION-BY-REFERENCE OF MATERIALS FILED ON COMPACT DISC

The present application includes a TABLE filed electronically via EFS-Web that includes a file named NS1A_F2F3. The table was last modified Dec. 1, 2006 at 4:49 PM and includes 252,952 bytes.

BACKGROUND OF THE INVENTION

Without limiting the scope of the invention, its background is described in connection with Influenza virus.

Influenza A and B viruses cause a highly contagious respiratory disease in humans resulting in approximately 36,000 deaths in the United States annually (Wright and Webster, 2001; Prevention, 2005). These annual epidemics also have a large economic impact, and cause more than 100,000 hospitalizations per year in the United States alone. Influenza A viruses, which infect a wide number of avian and mammalian species, are responsible for the periodic widespread epidemics, or pandemics, that have caused high mortality rates (Wright and Webster, 2001). The most devastating pandemic occurred in 1918, which caused an estimated 20 to 40 million deaths worldwide (Reid et al., 2001). Less devastating pandemics occurred in 1957 and 1968. Influenza B virus infections comprise about 20% of the yearly cases, but influenza B virus, which appears to infect only humans, does not cause pandemics (Wright and Webster, 2001).

Influenza A and B viruses contain negative-stranded RNA genomes, which are in the form of eight RNA segments (Lamb and Krug, 2001). Most, but not all, of the corresponding genome RNA segments of influenza A and B viruses encode proteins of similar functions. Here we will focus on influenza A virus. The three largest genome segments encode the three subunits of the polymerase, PB1, PB2 and PA. The segment encoding PB1 also encodes a small nonstructural protein, PB1-F2, which has apoptotic functions. The middle-sized segments encode the hemagglutinin (HA), the nucleocapsid protein (NP) and the neuraminidase (NA). HA, the major surface protein of the virus, binds to sialic acid-containing receptors on host cells, and is the protein against which neutralizing antibodies are produced. NP protein molecules are bound at regular intervals along the entire length of each of the genomic RNAs to form ribonucleoproteins (RNPs), and also have essential functions in viral RNA replication. The NA viral surface protein removes sialic acid from glycoproteins. One of its major functions is to remove sialic acid during virus budding from the cell surface and from the HA and NA of the newly assembled virions, thereby obviating aggregation of the budding virions on the cell surface. The seventh genomic RNA segment encodes two proteins, M1 (matrix protein) and M2. The M1 protein underlies the viral lipid membrane, and is thought to interact with the genomic RNPs and with the inner (cytoplasmic) tails of the surface proteins, e.g., HA and NA. The M2 protein is an ion channel protein that is essential for the uncoating of the virus. The smallest segment encodes two proteins, NS1A and NS2. The NS2 protein mediates the export of newly synthesized viral RNPs from the nucleus to the cytoplasm. The NS1A protein is a multi-functional protein not that is not incorporated into virion particles (hence the designation "non structural"), and is discussed below.

The primary means for controlling influenza virus epidemics has been vaccination directed primarily against HA (Wright and Webster, 2001). However, the antigenic structure of the HA of influenza A virus can undergo two types of change (Wright and Webster, 2001). Antigenic drift results from the selection of mutant viruses that evade antibodies directed against the major antigenic type of the HA circulating in the human population. Mutant viruses are readily generated because the viral RNA polymerase has no proof-reading function. Because of antigenic drift, the vaccine has to be reformulated each year. Antigenic shift in HA results from reassortment of genomic RNA segments between human and avian influenza A virus strains, resulting in a new (potentially pandemic) virus encoding a novel avian-type HA that is immunologically distinct. The human population has little or no immunological protection against such a new virus. The viruses containing the H2 and H3 HA subtypes that caused pandemics in 1957 and 1968, respectively, resulted from the reassortment of avian and human genomic RNA segments (Wright and Webster, 2001). The HA of influenza B viruses undergoes antigenic drift, but not antigenic shift, because influenza B viruses do not have non-human hosts.

Pandemic influenza A viruses can also apparently arise by a different mechanism. It has been postulated that the 1918 H1 pandemic strain derived all eight genomic RNAs from an avian virus, and that this virus then underwent multiple mutations in the process of adapting to mammalian cells (Reid et al., 2004; Taubenberger et al., 2005). H5N1 viruses, which have already spread from Asia to Europe and Africa, appear to be undergoing this route for acquiring pandemic capability (Horimoto and Kawaoka, 2005; Noah and Krug, 2005). These viruses, which have been directly transmitted from chickens to humans, contain only avian genes, and are highly pathogenic in humans. The human mortality rate has been high, approximately 55% (WHO, 2006). H5N1 viruses have not yet acquired the ability for efficient transmission from humans to humans. Recent studies indicate that efficient human transmission will require more than the acquisition of the ability of HA to bind to human sialic acid receptors in the upper respiratory tract of mammalian organisms (Maines et al., 2006). However, at least one H5N1 gene, the PB2 gene, has already undergone adaptation to mammalian cells (Hatta et al., 2001). The vast majority of pathogenic H5N1 viruses have acquired a lysine at position 627 in the PB2 protein, in place of the glutamic acid that is found at this position in avian viruses. The presence of lysine at this position apparently enhances virus replication in mammalian cells, but the mechanism of enhancement has not been established (Crescenzo-Chaigne et al., 2002; Shinya et al., 2004).

Effective control of a H5N1 pandemic will require the use of antiviral drugs because it is not likely that sufficient amounts of an effective vaccine will be available, particularly in the early phase of a fast-spreading pandemic (Ferguson et al., 2005; Longini et al., 2005; Ferguson et al., 2006; Germann et al., 2006). Antivirals can be stockpiled, and if appropriately used, should limit the spread of pandemic influenza virus. The strategies that have been proposed for the use of antivirals to stem a H5N1 pandemic would also be expected to lead to more effective use of antivirals during annual influenza epidemics. Currently, there are two classes of antiviral drugs. One class, amantadine/rimantidine, is directed against the M2 ion channel of influenza A viruses (Pinto et al., 1992; Wang et al., 1993; Chizhmakov et al., 1996). Virus mutants resistant to this class of drugs rapidly emerge (Cox and Subbarao, 1999; Suzuki et al., 2003), and many of the human isolates of H5N1 viruses are already resistant to these drugs (Puthavathana et al., 2005). The other class of drugs is directed at NA, and is effective against both influenza A and B viruses (von Itzstein et al., 1993; Woods et al., 1993; Ryan et al., 1994; Gubareva et al., 1995; Kim et al., 1997; Mendel et al., 1998). However, H5N1 viruses that are partially, or completely, resistant to the NA inhibitor oseltamivir have been reported (de Jong et al., 2005; Le et al., 2005). The emergence of H5N1 viruses to these two classes of antiviral drugs highlights the need for additional antiviral drugs against influenza virus.

SUMMARY OF THE INVENTION

The present invention includes the structure and function of the cellular polyadenylation and specificity factor 30 (CPSF30) binding site, or "binding epitope", on the surface of the influenza A non-structural protein 1 (NS1). When referring to influenza A, the protein is referred to herein as NS1A. The NS1 protein of influenza A virus will be designated as the NS1A protein to distinguish it from the NS1 protein encoded by influenza B virus, which will be designated as the NS1B protein. Several fragments of the NS1A protein were identified, from various influenza strains, that provide high-level expression and solubility in E. coli expression systems. The present invention also includes expression systems and protocols for producing large quantities of the previously identified F2F3 fragment of human CPSF30, which binds to the NS1A effector domain (Twu et al., 2006). These fragments of the NS1A protein and of CPSF30 provide high quality NMR spectra, suitable for lead compound optimization. Combining these reagents and information, we have designed a gel filtration assay suitable for characterizing complex formation between NS1A and CPSF30 (or fragments thereof), as well as a fluorescence polarization (FP) assay of NS1A —CPSF30 interactions that is suitable for high throughput screening for lead compounds to develop antiviral drugs. Using these reagents, complexes of the tetrameric complex between the NS1A effector domain and F2F3 were also generated. We have also developed a process for crystallizing this complex. These crystals were used to determine the 3D structure of the NS1A effector domain: F2F3 complex, and to definitively identify for the first time all the NS1A amino acids that comprise a portion of the CPSF30 binding epitope in the NS1A protein. These reagents and structural data, together with specific site-directed mutagenesis data, have allowed us to define a structure-based process for high-throughput screening of inhibitors and lead optimization that will allow development of influenza A antiviral drugs. Also disclosed is a process using these reagents and structural data to develop attenuated strains of influenza A suitable for use as animal (e.g. avian) or human vaccines.

Using the present invention it is possible for antiviral drug(s) to be directed at a viral target that differs from that of currently available influenza antivirals. Novel approaches are important because influenza A viruses, including avian influenza virus, are developing resistance to existing antiviral drugs. The present invention also describes a process for developing vaccines using structural information that has not been previously disclosed. A vaccine using live attenuated strains of influenza A virus is expected to provide better protection than a vaccine using inactivated virus. The present invention may also be used to develop, isolate and characterize antiviral drugs and live attenuated virus vaccine for both seasonal and pandemic influenza virus infections.

More particularly, the present invention includes a complex of the F2F3 fragment of CPSF30 with the portion of the NS1A protein of influenza A virus comprising amino acid residues 85 to 215 (NS1A (85-215)). The complex can be used in a method of identifying an inhibitor of influenza A virus by preparing a reaction system comprising at least a portion of NS1A of an influenza A virus, the F2F3 fragment of CPSF30, and a candidate compound; and detecting binding between the at least a portion of NS1A and F2F3, wherein reduced binding in the presence of the candidate drug relative to the control is indicative of activity of the compound against influenza virus. Examples of the NS1A fragments are listed in Table 2, and may also include the full length NS1A, and mutations thereof. The skilled artisan will recognize that the NS1A protein fragment may be prepared from other strains of influenza A viruses, e.g., human influenza A virus, a bovine influenza A virus, an equine influenza A virus, a porcine influenza A virus, an avian influenza A virus, an avian H5N1 viral strain.

For use with the present invention, the CPSF30 may be, e.g., a full length CPSF30, F3 zinc-finger domain, an F2F3-F2F3 tandem duplex, an F1F2F3 fragment, a soluble fragment of CPSF30, combinations and mutants thereof. Detection of the binding may be by, e.g., a high throughput screening assay, X-ray crystallography, nuclear magnetic resonance, analytical gel filtration, and combinations thereof. Other methods of detecting the interaction of the NS1A and CPSF30 (or portions thereof) may be, e.g., fluorescence resonance energy transfer, fluorescence polarization, immunofluorescence, chemiluminescence, radioimmunoassays, enzyme linked immunosorbent assays, mass spectrometry, and combinations thereof. For example, fluorescence polarization may use either a fluorescent labeled CPSF30, variant or fragment thereof or a fluorescent labeled NS1A protein, variant or fragments thereof.

The present invention also includes a process for using 3D (three-dimensional) information of the CPSF30 binding epitope on the influenza A virus NS1A protein for identifying inhibitors of an influenza A virus by obtaining concurrently the coordinates for the molecular position of at least a portion of an influenza NS1A protein and at least a portion of a CPSF30 protein and designing a molecule that will fit between the influenza NS1A protein and the CPSF30 protein based on the coordinates. The portion of the NS1A protein and the portion of the CPSF30 protein will generally be selected to provide high quality NMR spectra, e.g., the NS1A (85-215) fragment and the F2F3 fragment may be selected to form a tetrameric complex. In another example, the NS1A (85-215) fragment and the F2F3 fragment may form a tetrameric complex that is crystallized. Other examples may use an NS1A (85-215) fragment and the F2F3 fragment form a tetrameric complex that is crystallized and is used to determine the 3D structure of the NS1A (85-215):F2F3 complex using X-ray crystallography. The method may also include the step of identifying the NS1A amino acids that constitute the CPSF30 binding portion of the NS1A protein.

Yet another embodiment is a method of designing an inhibitor compound of an influenza A virus based on computational methods, wherein the inhibitor that binds at least one residue within the set of residues corresponds to the structure, using the crystal structure and its coordinates. The design method may be facilitated by using NMR spectra of samples of NS1A protein fragments, NMR spectra of samples of NS1A (85-215) or equivalent constructs thereof. The method may further include the step of optimizing the design of the molecule that fits between the NS1A (85-215) protein and the CPSF30 protein using X-ray crystallography, and synthetic chemistry. The method of designing an inhibitor compound may also include step of optimizing the design of the molecule that fits between the NS1A (85-215) protein and the CPSF30 protein using X-ray crystallography, NMR, synthetic chemistry and combinations thereof. Another embodiment of method of designing an inhibitor compound may also include, optionally or in combination one or more of the following: modifying the F2F3 structure of CPSF30, or any substructure, based on its conformation bound to NS1A to rationally design one or more small molecule inhibitors; modifying the F2F3 structure of CPSF30, or any substructure, to rationally design one or more small molecule inhibitors based on its conformation bound to NS1A of the F2F3 aromatic rings, the sidechain of residue Lys101, or combinations thereof, modifying the F2F3 structure of CPSF30, or any substructure, to rationally design one or more small molecule inhibitors by virtual screening; using the three-dimensional structure of the NS1A binding pocket to select one or more small molecule inhibitors or using the three-dimensional structure of the NS1A binding pocket to select one or more small molecule inhibitors by virtual screening. Any fragments of, full length, and strains of NS1A, and fragments of, full length, and strains of CPSF30 and combinations thereof may be used in conjunction with the method of designing an inhibitor compound.

Another embodiment of the present invention includes a process for engineering a live attenuated influenza A virus vaccine by mutation of specific residues in the CPSF30-binding epitope of the NS1A protein based on the 3D structure of the complex formed between NS1A (85-215) and F2F3, a tetramer interface and combinations thereof. Specific examples of residues at the tetramer interface site include, e.g., F103, L105, M106 and equivalents thereof. Specific examples of residues at the CPSF30-binding epitope include, e.g., M106, K110, I117, I119, Q121, D125, V180, G183, G184, W187 and equivalents thereof. The process may further include mutating the double-strand RNA binding epitope.

Another embodiment of the present invention includes an attenuated influenza A virus vaccine that includes one or more of eight viral RNA segments, wherein a viral RNA segment eight has a first mutation that causes a substitution of a first amino acid corresponding to an amino acid of SEQ. ID. NO. 1 at a position F103, L105, M106, K110, I117, I119, Q121, D125, L144, V180, G183, G184, or W187; wherein the first mutation decreases the CPSF30 binding ability of the NS1A protein. In one embodiment, at least a second mutation anywhere in the NS1A protein. The vaccine may also include at least second mutation causes a substitution of at least a second amino acid corresponding to an amino acid of SEQ ID NO.: 1 at a position F103, L105, M106, K110, I117, I119, Q121, D125, L144, V180, G183, G184, W187 and equivalents thereof. Alternatively, the vaccine may also include at least second mutation with a substitution of at least a second amino acid corresponding to an amino acid of SEQ ID NO.: 1 at a position T5, P31, D34, R35, R38, K41, G45, R46, and T49 at a dsRNA binding epitope and equivalents thereof. Alternatively, the vaccine may also include at least second mutation with at least second mutation causes a substitution of at least a second and third amino acid corresponding to an amino acid of SEQ. ID. NO. 1 at a position T5, P31, D34, R35, R38, K41, G45, R46, and T49 at a dsRNA binding epitope and/or F103, L105, M106, K110, I117, I119, Q121, D125, L144, V180, G183, G184, W187 and equivalents thereof. The influenza virus is a may be a cold-adapted influenza virus and will generally be selected to elicit an immune response. Non-limiting examples of influenza virus that may be used to make the attenuated vaccine may be is selected from, e.g., a human influenza A virus, a bovine influenza A virus, an equine influenza A virus, a porcine influenza A virus, an avian influenza A virus, an avian H5N1 viral strain.

The present invention also includes a pharmaceutical composition having a live attenuated influenza A virus vaccine by mutation of specific residues in the CPSF30-binding epitope of the NS1A protein based on the 3D structure of the complex formed between NS1A (85-215) and F2F3, a tetramer interaction site and combinations thereof and a pharmaceutically acceptable carrier or diluent. The vaccine may be used in a method of prophylaxis of a disease condition caused by the influenza virus by administering to a subject in need thereof a therapeutically effective amount of a live attenuated influenza A virus vaccine by mutation of specific residues in the CPSF30-binding epitope of the NS1A protein based on the 3D structure of the complex formed between NS1A (85-215) and F2F3, a tetramer interaction site, the dsRNA binding epitope and combinations thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
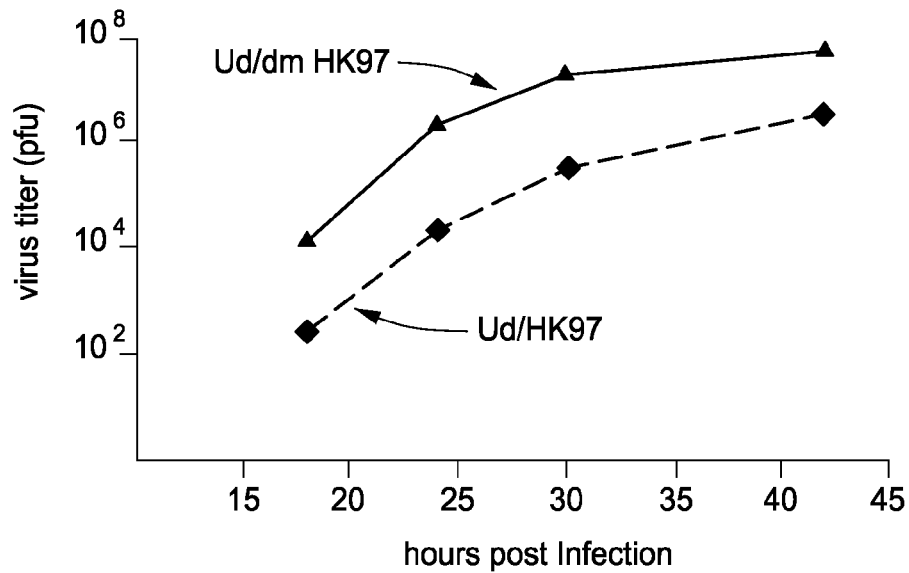
FIGS. 1A and 1B are graphs that show the effects on the growth of a recombinant influenza A virus resulting from mutations in its of mutations on NS1A protein that relate to the ability of the NS1A to bind to CPSF30.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

One of the best clues to a protein's function is its structure. The present invention takes advantage of structure-based bioinformatics platforms in "functional genomics." The structure-function data obtained from various structural determination may be used the isolation of novel biopharmaceuticals and/or drug targets from gene sequence information with greater efficiency. One way to identify the biochemical and medical function of a gene product is to determine its three-dimensional structure. Although there are numerous examples in which the primary (i.e., linear) structure of a protein has provided key clues to its biochemical function, three dimensional (3D) structure determination is considered to be more definitive at establishing biochemical function and mechanisms underlying these functions.

Protein structure. It is a generally accepted principle of biology that a protein's primary sequence is the main determinant of its tertiary structure. Anfinsen, Science 181:223-230 (1973); Anfinsen and Scheraga, Adv. Prot. Chem. 29:205-300 (1975); and Baldwin, Ann. Rev. Biochem. 44:453-475 (1975). For over a decade, researchers have been studying the theoretical and practical aspects of the folding of recombinant proteins.

Generally, proteins are composed of one or more autonomously-folding units known as domains. Kim, et al., Ann. Rev Biochem. 59:631-660 (1990); Nilsson, et al., Ann. Rev. Microbiol. 45:607-635 (1991). Multi-domain proteins in higher organisms are encoded by genes containing multiple exons and combinatorial shuffling of exons during evolution has produced novel proteins with different domain arrangements having different associated functions. Multi-domain protein may increase the ability of higher organisms to respond to environmental challenges because, via recombinational events, because the genomes may readily add, subtract, or rearrange discrete functionalities within a given protein. Patthy, Cell 41:657-663 (1985); Patthy, Curr. Opin. Struct. Bio. 4:383-392 (1994); and Long, et al., Science 92:12495-12499 (1995).

Interpretation of a protein structure. Several methods have been used to elucidate the 3D structure of a given protein molecule, e.g., X-ray crystallography and Nuclear Magnetic Resonance (NMR).

X-ray crystallography. X-ray crystallography is a technique that directly images molecules. A crystal of the molecule to be visualized is exposed to a collimated beam of monochromatic X-rays and the consequent diffraction pattern is recorded on a photographic film or by a radiation counter. The intensities of the diffraction maxima are then used to construct mathematically the three-dimensional image of the crystal structure. X-rays interact almost exclusively with the electrons in the matter and not the nuclei. The spacing of atoms in a crystal lattice can be determined by measuring the angle and intensities at which a beam of X-rays of a given wave length is diffracted by the electron shells surrounding the atoms. Operationally, there are several steps in X-ray structural analysis. The amount of information obtained depends on the degree of structural order in the sample. Blundell et al. provide an advanced treatment of the principles of protein X-ray crystallography. Blundell, et al., Protein Crystallography, Academic Press (1976), herein incorporated by reference. Likewise, Wyckoff et al. provide a series of articles on the theory and practice of X-ray crystallography. Wyckoff, et al. (Eds.), Methods Enzymol. 114: 330-386 (1985), relevant portions herein incorporated by reference. Important techniques for X-ray crystallography include methods for determining diffraction data phases by a multiple anomalous dispersion (MAD) method (described, for example, in Hendrickson, 1991), particularly using biosynthetic enrichment with seleno-methione (SeMet), and a molecular replacement method (described, for example, in Rossmann, M. G. The molecular replacement method. Acta Cryst. A46, 73-82 (1990).

Nuclear Magnetic Resonance (NMR). A general approach for the analysis of NMR resonance assignments was first outlined by Wuthrich, Wagner and co-workers. Wuthrich, "NMR of proteins and nucleic acids" Wiley, New York, N.Y. (1986); Wuthrich, Science 243:45-50 (1989); Billeter, et al., J. Mol. Biol. 155:321-346 (1982), relevant portions of each incorporated herein by reference. For a general review of protein determination in solution by nuclear magnetic resonance spectroscopy, see Wuthrich, Science 243:45-50 (1989); Billeter et al., J. Mol. Biol. 155:321-346 (1982). More recent improvements using multidimensional and triple resonance NMR methods (described, for example, in J. Cavanagh, W. Fairbrother, A. Palmer, and N. Skelton, Protein NMR Spectroscopy, Principles and Practice, 2ed Ed, Academic Press, NY, 2006, incorporated herein), familiar to someone trained in the art, are elaborations of these basic principles.

As used herein, the terms "CPSF30 binding epitope" or "CPSF binding site" refer to that portion of the NS1 protein of influenza that interacts with one or more zinc fingers of the CPSF30 protein.

As used herein, the terms "NS1A-binding epitope" or "NS1A binding site" refer to that portion of the CPSF30 protein that interacts with the NS1 protein of influenza A.

As used herein, the term "tetramer interface" refers to those portions of the NS1A protein and the CSPF30 protein that interact NS1A:CPSF30 complex, which can be a dimer or tetramer.

As used herein, the terms "double-strand RNA binding site" or "doubled-stranded RNA binding epitope" refer to that portion of the NS1A protein that interacts with double-stranded RNA, e.g., for suppressing host innate immune response. Greater structural details regarding the double-strand RNA binding site is taught by the present co-inventors in PCT/US2003/036,292, "Process for Designing Inhibitors of Influenza Virus Non-Structural Protein 1," relevant portions incorporated herein by reference and U.S. Provisional Patent Application Ser. No. 60/737,742, "Novel Compositions and Vaccines Against Influenza and Influenza B Infections," and PTC Patent Application Filed Nov. 17, 2006 "Novel Compositions and Vaccines Against Influenza and Influenza B Infections," relevant portions and tables incorporated herein by reference.

As used herein, the term "epitope" refers to a portion of a protein that is capable of interacting with the same or another protein and that can be define by atoms in amino acids in a linear sequence, by atoms in amino acids that are located throughout the protein (or subunits thereof) and that come together in three dimensions to form an interactive structure. The skilled artisan will recognize that an epitope may be a structure such as a "zinc finger," a portion of a molecular surface between two or more polypeptides that are capable of interacting, and/or a "binding pocket" or "enzymatic pocket" that lead to a function or interaction of the protein.

As used herein, the following nomenclature is used to define the zinc finger domains of the CPSF30 protein that interact NS1A, namely, "F1", "F2" and "F3" when referring to individual zinc fingers, "F1F2", "F2F3" when referring to a pair of zinc fingers and "F1F2F3" when referring to the three zinc fingers.

As used herein, the term "rationally design" refers to a series of steps for designing, e.g., initial small molecule inhibitors that may be further refined through medicinal chemistry and/or the selection of inhibitors that can be further modified chemically and that fit the molecular characteristics of a molecule that will meet the design criteria for modifying the interactions between or the activity of NS1A and CPSF30 based fully and/or at least in part on the three dimensional (3D) coordinates described herein.

As used herein, the term "virtual screening" refers to in silico design, using computer software to screen for possible binding ligands from a library of virtual molecules, allowing the characterization and refinement of small molecule inhibitors that will meet the design criteria for modifying the interactions between or the activity of NS1A and CPSF30 based fully and/or at least in part on the three dimensional (3D) coordinates described herein.

As used herein, the term "corresponding positions" refers to amino acids at that are generally in the same spatial location in the three-dimensional structures of homologous protein structures. In one example, a corresponding position is determined by 3D structure alignment using standard techniques known to a person skilled in the art, such as the PRISM program, described by Yang and Hong Yang, A.-S, and Honig, B. (2000) An Integrated Approach to the Analysis of Sequence and Structure. I. Protein Structural Alignment and a Quantitative Measure for Protein Structural Distance. J. Mol. Biol. 301: 665-678; Yang, A.-S, and Honig, B. (2000) An Integrated Approach to the Analysis of Sequence and Structure. III. A Comparative Study of Sequence Conservation in Protein Structural Families Using Multiple Structural Alignments, or the VISTAL program, described by Kolodny, R. and Honig, B. (2006) VISTAL—A New 2D Visualization Tool of Protein 3D Structural Alignments. Bioinformatics 22:2166-2167 (e.g., using the default settings for either), relevant portions incorporated herein by reference. The alignment may include the introduction of gaps in the sequences to be aligned. In the absence of 3D structures for protein pairs, corresponding positions may be identified (until such time that the requisite 3D structures are available) by sequence-based alignment using standard techniques known to a person skilled in the art, such as a Needleman-Wunsch dynamic programming algorithm (described in Needleman, S. B. and Wunsch, C. D., J Mol. Biol. 48: 443-453 (1970), a Gapped BLAST/PSI-BLAST algorithm (described in Altschul, et al Nucl. Acid. Res. 25: 3389-3402 (1997), or a CLUSTAL W/X multiple sequence alignment algorithm (described in Thompson, J. D., Higgins, D. G. and Gibson, T. J. (1994) CLUSTAL W: improving the sensitivity of progressive multiple sequence alignment through sequence weighting, position specific gap penalties and weight matrix choice. Nucl. Acid. Res. 22:4673-80 (1994).)(e.g., using the default settings for either relevant portions incorporated herein by reference. Corresponding position alignment(s) may also include the introduction of gaps in the sequences to be aligned.

Further examples of "corresponding positions are taught by the present co-inventors in PCT/US2003/036,292, "Process for Designing Inhibitors of Influenza Virus Non-Structural Protein 1," relevant portions incorporated herein by reference and U.S. Provisional Patent Application Ser. No. 60/737,742, "Novel Compositions and Vaccines Against Influenza and Influenza B Infections", and PTC Patent Application Filed Nov. 17, 2006 "Novel Compositions and Vaccines Against Influenza and Influenza B Infections,", relevant portions and tables incorporated herein by reference.

Non-limiting examples of numerous influenza A strains may be used with the present invention including those strains that are readily available or will become available as they emerge in human populations. Examples of influenza A strains for use and analysis with the present invention may include A/Memphis/8/88, A/Chile/1/83, A/Kiev/59/79, AAUdorn/307/72, A/NT/60/68, A/Korea/426/68, A/Great Lakes/0389/65, A/Ann Arbor/6/60, A/Leningrad/13/57, A/Singapore/1/57, A/PR/8/34, A/Vietnam/1203/04, A/HK/483/97, A/South Carolina/1/181918 (the 1918 pandemic virus H1N1 strain), and A/WSN/33. The sequences of these strains are available from GenBank, CDC and viral stock may be available from the American Type Culture Collection, Rockville, Md. or are otherwise publicly available.

As used herein, the term "variant" gene or protein refers to a gene or protein that differs from the wild type gene or protein by way of nucleotide or amino acid substitution(s), addition(s), deletion(s), and combinations thereof. Depending on the context, the term mutant is also used to describe variations from the wild-type sequence that are natural, introduced at random and/or introduced into a gene or protein sequence specifically. Likewise, a fragment is used to describe a fragment of the complete length of the translated polypeptide, whether natural or not. Often, the skilled artisan will design fragments that include or avoid certain amino acid that may affect, e.g., synthesis or cause steric hindrance or other design requirements. When designing alternate peptide constructs with enhanced anti-viral properties, substitutions may be used which modulate one or more properties of the molecule. Variants typically include the exchange of one amino acid for another at one or more sites within the peptide. For example, certain amino acids may be substituted for other amino acids in a peptide structure in order to enhance the interactive binding capacity of the structures. Certain amino acid substitutions can be made in a protein sequence (or its underlying DNA coding sequence) to create a peptide with superior functional characteristics. In particular, those changes that enhance the amphipathic, α-helical nature may be desired.

As used herein, the term “candidate compound” refers to any molecule that may inhibit influenza viral growth. The candidate substance may be a protein or fragment thereof, a small molecule, or even a nucleic acid molecule. Various commercial sources of small molecule libraries meet the basic criteria for useful drugs in an effort to “brute force” the identification of useful candidate compounds. Screening of such libraries, including libraries generated combinatorially (e.g., peptide libraries, aptamer libraries, small molecule libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds. Candidate compounds may be screened from large libraries of synthetic or natural compounds. One example of a candidate compound library is an FDA-approved library of compounds that can be used by humans. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.) and a rare chemical library is available from Aldrich (Milwaukee, Wis.). Combinatorial libraries are available or can be prepared. Alternatively, libraries of natural candidate compounds in the form of bacterial, fungal, plant and animal extracts are also available from, for example, Pan Laboratories (Bothell, Wash.) or MycoSearch (N.C.), or can be readily prepared by methods well known in the art. Candidate compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

The amino acid sequence of the NS1A protein of Influenza A virus, A/Udorn/72:

```
                                                             (SEQ ID NO.: 1)
  1 MDPNTVSSFQ VDCFLWHVRK RVADQELGDA PFLDRLRRDQ KSLRGRGSTL GLDIETATRA

61 GKQIVERILK EESDEALKMT MASVPASRYL TDMTLEEMSR EWSMLIPKQK VAGPLCIRMD

121 QAIMDKNIIL KANFSVIFDR LETLILLRAF TEEGAIVGEI SPLPSLPGHT AEDVKNAVGV

181 LIGGLEWNDN TVRVSETLQR FAWRSSNENG RPPLTPKQKR EMAGTIRSEV.
```

The anti-viral agents disclosed herein may be used in conjunction with methods to reduce virus growth, infectivity, burden, shed, development of anti-viral resistance, and to enhance the efficacy of traditional anti-viral therapies.

The amino acid sequence of the relevant fragments of human CPSF30 (UniProt id 095639):

```
                                                             (SEQ ID NO.: 13)
  1 MQEIIASVDH IKFDLEIAVE QQLGAQPLPF PGMDKSGAAV CEFFLKAACG          50

51 KGGMCPFRHI SGEKTVVCKH WLRGLCKKGD QCEFLHEYDM TKMPECYFYS         100

101 KFGECSNKEC PFLHIDPESK IKDCPWYDRG FCKHGPLCRH RHTRRVICVN         150

151 YLVGFCPEGP SCKFMHPRFE LPMGTTEQPP LPQQTQPPAK QSNNPPLQRS         200

201 SSLIQLTSQN SSPNQQRTPQ VIGVMQSQNS SAGNRGPRPL EQVTCYKCGE         250

251 KGHYANRCTK GHLAFLSGQ
```

The amino acid sequence of the relevant fragments of human CPSF30 discussed in this patent are:

F1 Zn-Finger Domain: residues 41-59;
F2 Zn-Finger Domain: residues 68-86;
F3 Zn-Finger Domain: residues 96-114;
F4 Zn-Finger Domain: residues 124-142;
F5 Zn-Finger Domain: residues 148-166; and
F5 Zn-Finger Domain: residues 243-260.

As used herein F2F2 are residues 61-121 of SEQ ID NO.: 13:

```
 61 SGEKTVVCKH WLRGLCKKGD QCEFLHEYDM TKMPECYFYS 100

101 KFGECSNKEC PFLHIDPESK I                     121
```

As used herein F1F2F3 are residues 39-121 of SEQ ID NO.: 13:

```
 39 AV CEFFLKAACG                                           50

51 KGGMCPFRHI SGEKTVVCKH WLRGLCKKGD QCEFLHEYDM TKMPECYFYS 100

101 KFGECSNKEC PFLHIDPESK                                  121
```

The anti-viral properties of the peptides disclosed herein allow them to be included in formulations to inhibit virus growth and proliferation. The purified anti-viral peptides may be used without further modifications or they may be diluted in a pharmaceutically acceptable carrier. The invention may be administered to humans or animals, included in food and pharmaceutical preparations. They anti-viral agents may also be used in medicinal and pharmaceutical products (such as fluid containers, iv. bags, tubing, syringes, etc.), as well as in cosmetic products, hygienic products, cleaning products and cleaning agents, as well as any material to which the peptides could be sprayed on or adhered to wherein the inhibition of virucidal growth on such a material is desired.

The dosage of an anti-viral peptide necessary to prevent viral growth and proliferation depends upon a number of factors including the types of virus that might be present, the environment into which the peptide is being introduced, and the time that the peptide is envisioned to remain in a given area.

As used herein, the phrases "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active antiviral agents of the present invention may be formulated into classic pharmaceutical preparations and administered via any common route so long as the target tissue is available via that route. These routes of administration include, e.g., oral, alveolar, nasal, buccal, rectal, vaginal or topical. In particular, use of the anti-viral peptides of the present invention in a condom or diaphragm, optionally in conjunction with a spermicidal or other contraceptive substance, is envisioned. Alternatively, administration may be orthotopic, intradermal, subcutaneous, intramuscular, intraperitoneal or intravenous. The antiviral agent may also be administered parenterally or intraperitoneally. Solutions of the antiviral agent may be compounded into a free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antiviral agent(s) will generally be provided in a pharmaceutical dosage form suitable for injectable use, e.g., sterile aqueous solutions or dispersions and sterile powders for the extemporaneous preparation of sterile injectable solutions or dispersions. For widespread use, the antiviral agents may be stable under the conditions of manufacture and storage and must be preserved against the contaminating action of microorganisms, such as bacteria and fungi. The antiviral agents will commonly be provided with a carrier, e.g., a solvent or dispersion medium that may include, e.g., water, ethanol, polyol (for example, glycerol, propylene glycol, and liquid polyethylene glycol, and the like), suitable mixtures thereof, and vegetable oils. Proper dosage fluidity can be maintained, for example, by the use of a coating, such as lecithin, by the maintenance of the required particle size in the case of dispersion and by the use of surfactants. The prevention of the action of microorganisms can be brought about by various antibacterial and/or antifungal agents, for example, parabens, chlorobutanol, phenol, sorbic acid, thimerosal, and the like. In many cases, the dosage form will include isotonic agents, e.g., sugars or sodium chloride. Prolonged absorption of the injectable compositions can be brought about by the use in the compositions of agents delaying absorption, for example, aluminum monostearate and gelatin.

Generally, sterile injectable solutions are prepared by incorporating the active compounds in the required amount in the appropriate solvent with various of the other ingredients enumerated above, as required, followed by sterilization. Generally, dispersions are prepared by incorporating the various sterilized active ingredients into a sterile vehicle that includes the basic dispersion medium and the required other ingredients from those enumerated above. Preparation of sterile powders for injectable solutions maybe prepared by, e.g., vacuum-drying, spray-freezing, freeze-drying or other techniques that yield a powder of the active ingredient plus any additional desired ingredient from a previously sterile-filtered solution thereof.

As used herein, a "pharmaceutically acceptable carrier" refers to solvents, dispersion media, coatings, antibacterial and anti-fungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration, the antiviral agent(s) of the present invention may be incorporated with excipients and used in the form of ingestible or non-ingestible mouthwashes and dentifrices. A mouthwash may be prepared incorporating the active ingredient in the required amount in an appropriate solvent, such as a sodium borate solution (Dobell's Solution). Alternatively, the antiviral agent(s) may be incorporated into an antiseptic wash containing sodium borate, glycerin and potassium bicarbonate. The antiviral agent(s) may also be dispersed in dentifrices, e.g., gels, pastes, powders and slurries. The antiviral agent(s) may be added in a therapeutically effective amount to a paste dentifrice that may include water, binders, abrasives, flavoring agents, foaming agents, and humectants.

The antiviral agent(s) may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric and the like. Salts may also be formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, the antiviral agent(s) will be administered in a manner compatible with the dosage formulation and in such amount as is therapeutically effective. The formulations are easily administered in a variety of dosage forms such as injectable solutions, drug release capsules and the like. Sterile aqueous media that can be employed will be known to those of skill in the art in light of the present disclosure, e.g., Remington: The Science and Practice of Pharmacy, 21st Edition, Lippincott Williams & Wilkins (2005), relevant portions incorporated herein by reference. Some variation in dosage will necessarily occur depending on the condition of the subject being treated for which the skilled artisan will determine the appropriate dose for the individual subject. Moreover, for human administration, preparations should meet sterility, pyrogenicity, general safety and purity standards as required by FDA Office of Biologics standards.

In one embodiment, the vaccine comprises a pharmaceutically acceptable vehicle. The suitable vehicles may be both aqueous and non-aqueous. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, immunostimulants, immunosuppressants, wetting agents, emulsifying and suspending agents, or any combination thereof.

Examples of suitable adjuvants include, without limitation, incomplete Freund's adjuvant, aluminum phosphate, aluminum hydroxide, or alum, Stimulon® QS-21 (Aquila Biopharmaceuticals, Inc., Framingham, Mass.), MPL® (3-0-deacylated monophosphoryl lipid A; Corixa, Hamilton, Mont.), and interleukin-12 (Genetics Institute, Cambridge, Mass.).

A person of the ordinary skill in the art has a sufficient expertise to determine the dosage of the vaccines of the instant invention. Such dosage depends on the pathogenicity of the virus included in the vaccine and on the ability of the antigen to elicit an appropriate immune response. In different embodiments of the invention, a virus vaccine composition of the instant invention may comprise from about $10^2$-$10^9$ plaque forming units (PFU)/ml, or any range or value therein (e.g., $10^3$, $10^4$, $10^5$, $10^6$, $10^7$, or $10^8$) where the virus is attenuated. A vaccine composition comprising an inactivated virus can comprise an amount of virus corresponding to about 0.1 to 200 μg of the amino acid sequences of the instant invention per ml, or any range or value therein.

The vaccines of the instant invention can be applied in multiple ways. According to one embodiment of the invention, the intranasal administration is via the mucosal route. The intranasal administration of the vaccine composition can be formulated, for example, in liquid form such as, for example, nose drops, spray, or suitable for inhalation. In other embodiment, the vaccine may be administered as a powder, or a cream, or an emulsion.

In another embodiment, the vaccines of the instant invention are applied by an injection, including, without limitation, intradermal, transdermal, intramuscular, intraperitoneal and intravenous. According to another embodiment of the invention, the administration is oral and the vaccine may be presented, for example, in the form of a tablet or encased in a gelatin capsule or a microcapsule, which simplifies oral application. The production of these forms of administration is within the general knowledge of a technical expert.

As used herein, "detectable labels" refer to compounds and/or elements that can be detected due to their specific functional properties and/or chemical characteristics, the use of which allows the agent to which they are attached to be detected, and/or further quantified if desired, such as, e.g., an enzyme, an antibody, a linker, a radioisotope, an electron dense particle, a magnetic particle or a chromophore. The detectable label may be half of a fluorescence resonance energy transfer (FRET) pair (for FRET variations see, e.g., U.S. Pat. No. 6,593,091, issued to Keys, relevant portions incorporated herein by reference). There are many types of detectable labels, including fluorescent labels, which are easily handled, inexpensive and nontoxic. Another example of a detection method relies on hydrogel-coated donor and acceptor beads providing functional groups for conjugation to biomolecules. AlphaScreen® by Berthold Technologies (Bad Wildbad, Germany)(Rouleau, N., Turcotte, S., Mondou, M. H., Roby, P. & Bosse, R. (2003) J Biomol Screen 8, 191-7.).

The present inventors recognized that certain regions of the NS1A protein can be targeted for the development of antiviral drugs. The NS1A protein is a multi-functional dimeric protein that participates in both protein-RNA and protein-protein interactions (Krug et al., 2003). The effector domain, which comprises the C-terminal two-thirds of the NS1A protein, contains the binding site for the 30-kDa subunit of the cellular cleavage and polyadenylation specificity factor (CPSF30) (Nemeroff et al., 1998; Li et al., 2001). This interaction results in the inhibition of 3' end processing of all cellular pre-mRNAs in infected cells, and as a consequence the production of mature mRNAs encoding antiviral proteins (such as interferon, IFN) is severely inhibited during infection (Shimizu et al., 1999; Kim et al., 2002; Noah et al., 2003). This inhibition is crucial to viral replication and spread, because influenza A virus, like several other RNA viruses (Yoneyama et al., 2004; Sumpter et al., 2005; Seth et al., 2006), efficiently activates the RIG-I RNA helicase and thereby triggers both the activation of IRF-3 and NF-kB and the synthesis of IFN-beta and other antiviral pre-mRNAs (Geiss et al., 2002; Kim et al., 2002; Siren et al., 2006). A recombinant influenza A/Udorn/72 virus expressing a NS1A protein with a mutated binding epitope for CPSF30 induced high levels of IFN-beta mRNA during infection and was highly attenuated (100-1000-fold) (Noah et al., 2003; Twu et al., 2006). A 61-amino-acid domain of CPSF30, comprising two of its zinc fingers (i.e., the F2F3 fragment), was found to bind efficiently to the NS1A protein (Twu et al., 2006). The expression of the F2F3 domain in cells leads to the inhibition of influenza A virus replication and increased production of IFN-beta mRNA, indicating that F2F3 likely blocks the binding of endogenous CPSF30 to the NS1A protein (Twu et al., 2006). These results validate the binding epitope on NS1A for CPSF30 as a potential target for the development of small molecule antiviral drugs directed against influenza A virus and as a target for engineering strains of virus that can be used as live attenuated vaccines.

Previous studies showed that residues 184-188 in the protein sequence of the NS1A protein are required for functional binding of CPSF30 (Li et al., 2001; Noah et al., 2003). Thus, this region is required for the binding of CPSF30 in vitro (Li et al., 2001), and mutation of amino acids 184-188 in the NS1A protein of a recombinant Udorn virus results in high attenuation coupled with increased synthesis of IFN-beta (Noah et al., 2003). These data demonstrate that this binding epitope is essential for virus replication. As shown by the structural studies described below, the 184-188 region of the NS1A protein sequence constitutes a subset of the CPSF30 binding epitope, observed in the 3D structure of the complex between NS1A effector domain and F2F3 which is disclosed for the first time in this Disclosure.

Figure 1B:
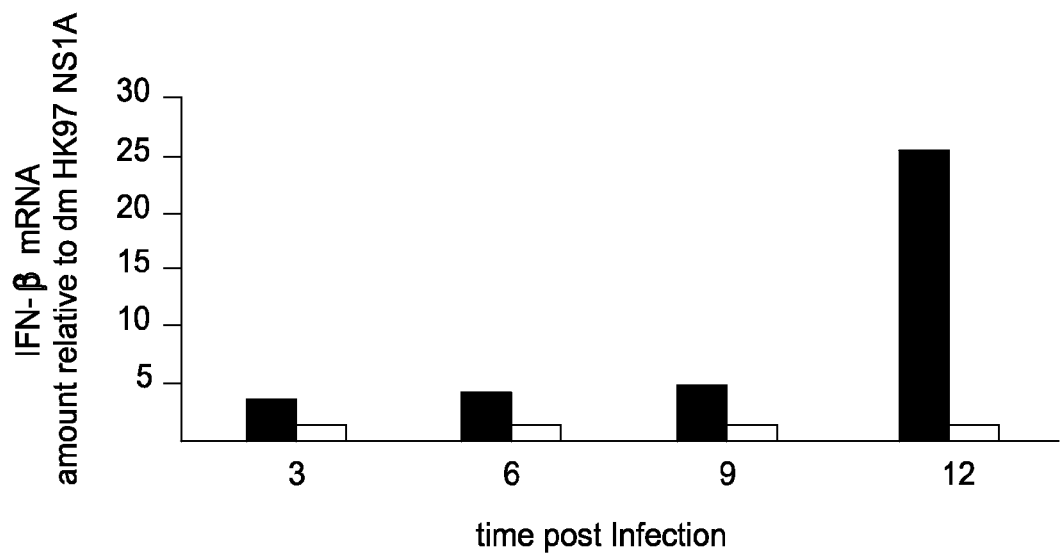

Studies with the NS1A proteins of H5N1 viruses established that the Met (M) residue at position 106 is required for functional F2F3/CPSF30 binding. We showed that the NS1A protein encoded by a pathogenic H5N1 virus that was transmitted to humans in 1997 (A/HK/483/97; HK97) lacks a binding epitope for CPSF30, whereas the NS1A protein encoded by a pathogenic 2004 H5N1 virus (A/Vietnam/1203/04; VN04) has acquired this binding epitope. We were able to generate a CPSF30 binding epitope in the HK97 NS1A protein by changing two of its amino acids to the corresponding amino acids in the VN04 NS1A protein, specifically by changing I at position 106 to M and L at 103 to F. To determine the effects of these two amino acid changes in the HK97 NS1A protein during virus infection, a recombinant Udorn virus was generated in which the Udorn NS gene was replaced by a HK97 NS gene encoding a NS1A protein with these two mutations (Ud/dmHK97 recombinant). The recombinant virus was then compared to the recombinant Ud virus containing the wild-type HK97 NS gene (Ud/HK97 recombinant). During multiple cycle growth the rate of replication and virus yield of the Ud/dmHK97 recombinant was 100-fold greater than with the Ud/HK97 recombinant virus (FIG. 1A), and is thus similar to the Udorn parent virus. During single-cycle growth, the Ud/HK97 virus induced a high level of IFN-beta mRNA production, which was almost completely suppressed in the cells infected by the Ud/dmHK97 virus (FIG. 1B). Most importantly, the replication of the Ud/dmHK97 virus was inhibited in F2F3-expressing cells (data not shown), indicating that the dmHK97 NS1A protein binds F2F3 in infected cells. The roles of Phe at 103 and the Met at 106 in the NS1A protein in forming the F2F3/CPSF30 complex is elucidated by the herein disclosed X-ray crystal structure of the NS1A:F2F3 complex, which reveals that amino acids 103 and 106 are required for CPSF30 binding because their hydrophobic interactions stabilize a tetrameric structure of the NS1A:F2F3 complex (see below). It should also be emphasized that essentially all (>98%) of the influenza A viruses (H3N2, H2N2 and H1N1) that have been isolated from humans, including the 1918 H1N1 virus, and include M and F at positions 106 and 103 in their NS1A proteins, respectively, indicating that these two amino acids, which are critical for CPSF30 binding and the resulting suppression of the production of IFN-0 mRNA, are conserved in human influenza A viruses. Accordingly, the tetrameric complex described in this disclosure is anticipated to be critical for the CSPF30 binding function of all such human influenza A viruses.

EXAMPLE 1

Figure 2:
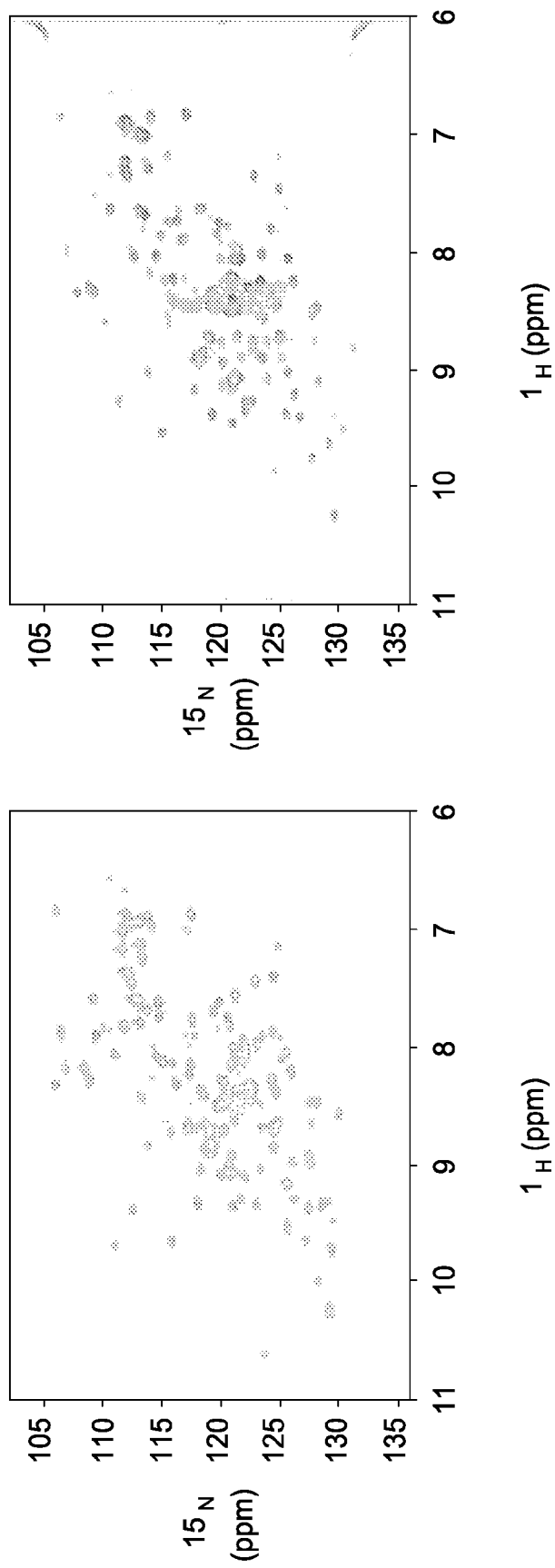
FIG. 2 shows NMR spectra of certain NS1A effector domains, demonstrating that such data can be used for structure-function analysis, inhibitor discovery and optimization, and in validating the effects of mutations on the structure of the effector domain.

Process for Discovering, Designing, and Optimizing Small Molecule Inhibitors of Influenza a Viruses, Including H5N1 Viruses Novel Reagents and Structural Data. To further delineate the interface between F2F3 of CPSF30 and the NS1A protein the inventors determined the three-dimensional (3D) structure of the tetrameric F2F3:NS1A complex. Ninety (90) different constructs (Table 2) were screened in order to find constructs suitable for crystallization and NMR analysis. These variants, summarized in Tables 3 and 4, included 8-11 different full-length or subsequences of NS1A with N-terminal (N-His) and C-terminal (C-His) affinity purification tags, prepared as described in Acton et al., 2005 from influenza A strains A/South Carolina/1/181918 (the 1918 pandemic virus H1N1 strain), HK97 (A/HK/483/97, 1997 Hong Kong), VN04 (A/Vietnam/1203/04, 2005 Vietnam), and Udorn (A/Udorn/72), respectively. These were assessed in terms of expression level and solubility (Tables 3 and 4), ability to purify, and biophysical properties, including 2D $^{15}N$—$^{1}H$ heteronuclear single quantum coherence correlation spectroscopy (HSQC). Many of these reagents, disclosed for the first time here, are useful for influenza A research purposes and for structural studies. The inventors focused on two specific constructs that provide particularly high expression and solubility, making them especially useful for biochemical and biophysical studies: the C-terminal hexaHis-tagged 85-215 amino acid fragments of the NS1A proteins from (i) influenza A/Udorn/72 (A/Udorn) and (ii) the H5N1 strain A/Vietnam/1203/04 (A/VN04). These highly soluble constructs can be produced in tens of milligram per liter quantities, and have been produced with SeMet labeling, for crystallography, and with $^{15}N$-enrichment for NMR studies. Excellent quality HSQC NMR spectra can be obtained for these two constructs in the pH range 5.5 to 6.5 (FIG. 2). Under these conditions, these constructs are of sufficiently good quality to indicate high feasibility for further NMR studies. They are also useful for small molecule screening studies. In addition, the F2F3 fragment of CPSF30 has been cloned into a pET expression vector with a N-terminal hexaHis tag (tag sequences are defined in Acton et al., 2005), produced with uniform $^{13}C$, $^{15}N$ enrichment, and complete backbone and sidechain resonance assignments have been determined using standard triple resonance NMR methods (Montelione et al., 1999). These NMR-optimized sample conditions and resonance assignments are useful for small molecule screening, lead optimization, and structure-function studies of F2F3:NS1A interactions.

Figure 3:
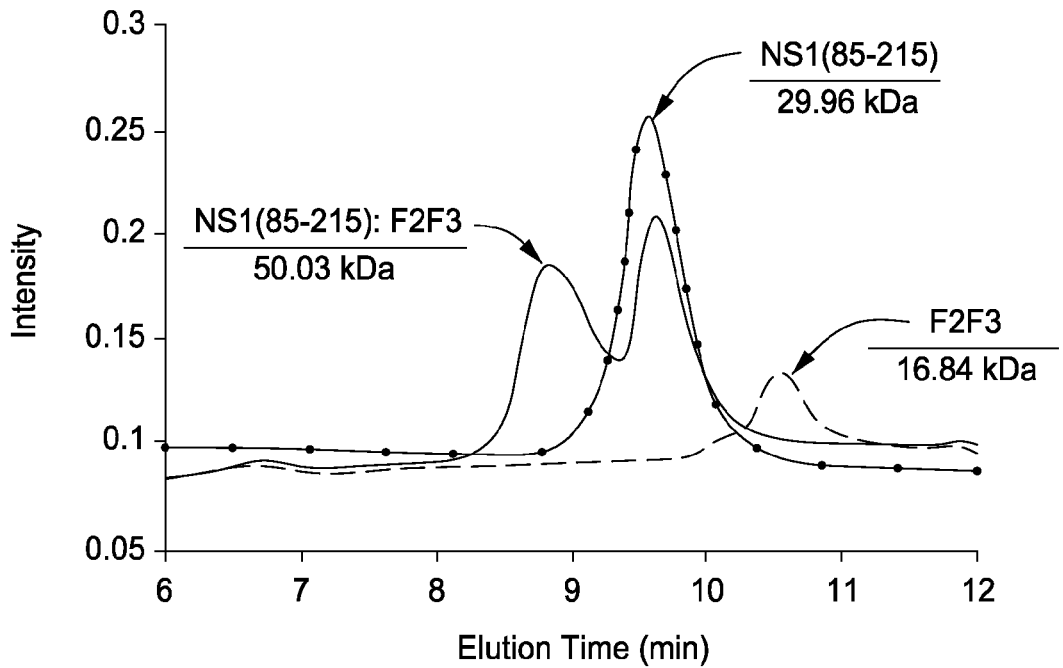
FIG. 3 shows the results from analytical gel filtrations assays of NS1A (85-215):F3F3 binding.

Because virus studies have used influenza A/Udorn/72 virus to identify CPSF30 binding activity during virus infection CPSF30 (Li et al., 2001; Noah et al., 2003), we have developed an assay for the binding of the NS1A Udorn effector domain to the F2F3 fragment of CPSF30 in vitro, using analytical gel filtration with detection of effluent by simultaneous refractive index and static light scattering measurements. The chromatography system used for this assay is described in Acton et al., 2005, in which it is used for other applications. In these studies, illustrated in FIG. 3, the NS1A Udorn (85-215) construct elutes as a dimer, with molecular weight of ~30 kDa. When this effector domain construct is first mixed with the 8.5 kDa F3F3 fragment, the resulting complex elutes with a molecular weight of ~50 kDa, indicating a stoichiometry of 2 F2F3: 2 NS1A effector domains. This gel filtration assay provides a convenient qualitative measure of F2F3 binding by NS1A effector domains.

Suitable samples of NS1A Udorn (85-215); the NS1A-Udorn(85-215):F2F3 complex, and other constructs listed in Table 2 and their complexes with F2F3 and CPSF30-derived constructs, can be produced and assessed using this gel filtration assay. These can then be crystallized for X-ray crystallographic analysis. Initial crystals of the NS1A-Udorn(85-215):F2F3 complex were obtained by high-throughput robotic screening using service facilities available through the Hauptman Woodward Res. Inst. (Buffalo N.Y.) (Luft et al., 2003; Acton et al., 2005). Crystallization optimization was then carried out for the NS1A-Udorn(85-215):F2F3 complex at Rutgers, yielding diffraction quality bi-pyramid crystal of size 0.15×0.15×0.25 mm³. Conditions providing crystals, and a description of these crystals, are presented herein below. Three-wavelength Se-Met multiple anomalous diffraction (MAD) (2.3 Å resolution) and a complete native (1.95 Å resolution) data sets were collected at X25 beam line at Brookhaven National Laboratories. The structure was solved by MAD techniques (Hendrickson, 1991) and refined to 1.95 Å resolution, and is currently refined to a R factor of 0.225 and R free of 0.245, respectively.

Crystallization of NS1A Udorn (85-215):F2F3 Complex. Initial crystallization conditions for NS1A Udorn (85-215):F2F3 complex were obtained by using robotic crystallization facility at the Buffalo facility described above. The most promising condition use 1.77 M potassium nitrate ($KNO_3$) at pH 5.0 as precipitant. This initial crystallization condition was optimized manually at Rutgers. Good quality crystals were obtained using 0.25-1.0 M $KNO_3$ and 10-20% sucrose/glucose as precipitant at pH 5-6. Diffraction quality crystals were obtained when P94S mutant F2F3 was used in the complex, though similar conditions are expected to provide crystals of the complex with the wild-type (P94) F2F3 sequence. The NS1A Udorn (85-215):F2F3 complex was crystallized with the symmetry of the space group $P4_1$ with cell parameters a=b=50.96, c=205.39 Å and α=β=γ=90°. A variant used in the X-ray crystal structure determination of NS1(85-215):F2F3 complex has Ser in place of Pro at position 94.

Figure 4A:
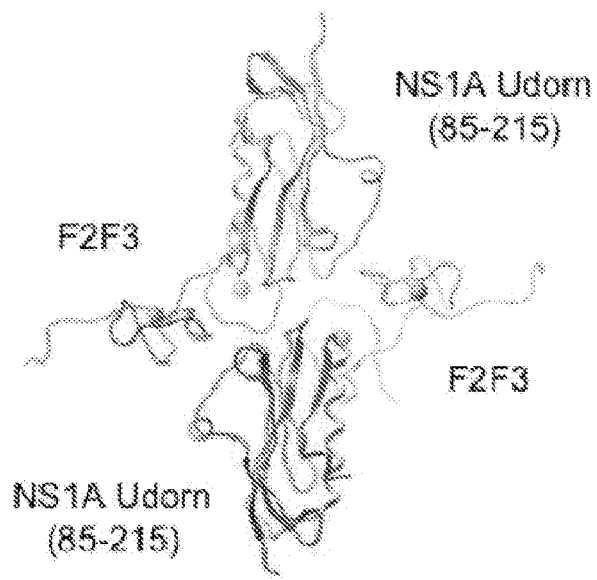
FIG. 4A shows the X-ray crystal structure of a tetrameric NS1A effector domain and F2F3.
Figure 4B:
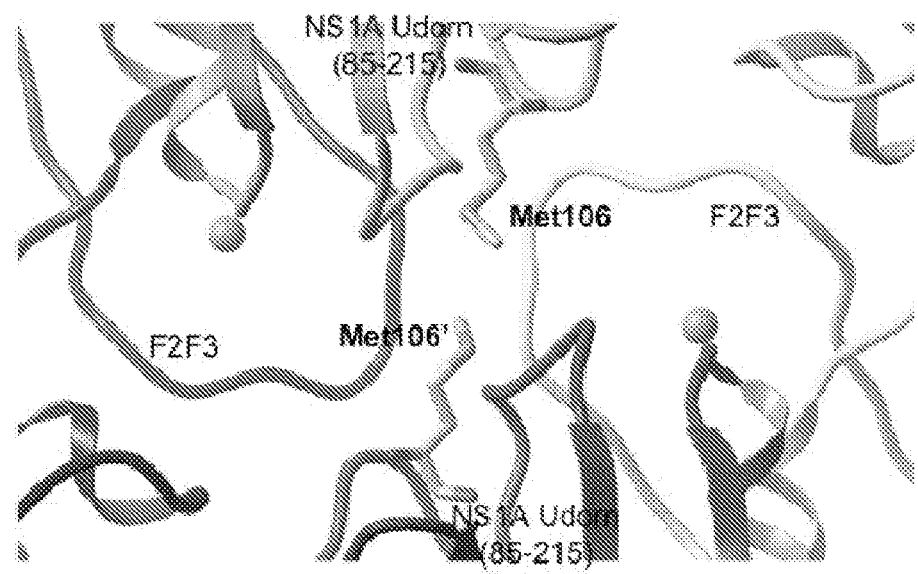
FIG. 4B shows the X-ray crystal structure for the Met106 residue in the core of the tetrameric NS1A (85-215):F2F3 complex.

FIGS. 4A and 4B disclose the crystal structure of the Udorn NS1A effector domain (residues 85-215) bound to the F2F3 fragment of CPSF30. Consistent with gel filtration data, the complex forms a tetrameric complex, in which two F2F3 molecules bridge two NS1A effector domains. The structure reveals for the first time the novel spatial arrangement of the subunits in the 2 NS1A: 2 F2F3 complex. This tetrameric arrangement was completely unexpected and novel.

Key residues Met106/Met106' of NS1A are packed in the core of the tetrameric interface or "tetramerization epitope," explaining its critical role in CPSF30 binding, as discussed above. However, while Met 106/Met106' are at the core of the tetrameric complex, they are not part of the primary F2F3/CPSF30 binding pocket. F1G. 5 illustrates the F2F3 binding pocket on the surface the Udorn NS1A effector domain. Specific interactions in this primary binding pocket involve residues K110, I117, I119, Q121, V180, G183, G184, and W187 of NS1A and residues F97, F98, F103, and K110 of the F3 finger of CPSF30. It should be noted that these residues include not only amino acids in, or adjacent to, the 184-188 sequence previously identified as part of the CPSF30 binding epitope by mutagenesis studies, but also amino acids in other regions in the NS1A protein not previously recognized to be essential for CPSF30 binding. Mutation of residues G183 or G184 in NS1A (85-215) each to Arg or Asp disrupts or reduces F2F2 binding affinity and/or tetramer formation, based on analytical gel filtration measurements without significantly disrupting the native structure of NS1A (85-215) indicated by $^{15}N$—$^1H$ HSQC NMR spectra (data not shown), demonstrating a functional role of these sites within the CPSF30 binding epitope of NS1A. Recombinant Udorn viruses encoding NS1A proteins in which either G184 or W187 was changed to Arg are attenuated (data not shown), further demonstrating that these amino acids are required for virus replication. The eight residues in the CPSF30-binding epitope of NS1A (FIG. 5) are almost 100% conserved amongst influenza A viruses isolated from humans (Macken et al., 2001), except for Ile 117 which is frequently replaced by Met. Based on this structure, disclosed for the first time here, we propose disruption of 2NS1A:2F2F3 tetramerization as a strategy to inhibit influenza A virus in human. Based on our structural data, we further propose that a small molecule inhibitor that binds tightly to the above described conserved epitope and surrounding regions will disrupt CPSF30 binding and will inhibit influenza A virus in humans. This pocket on the surface of the NS1A effector domain is the target of our proposed drug discovery process.

Table 1 describes some of the specific location of the epitopes described herein as the tetramerization, RNA binding and CPSF30 binding epitopes of NS1A.

TABLE 1

Tetramerization, RNA binding and CPSF30 binding epitopes of NS1A.

| NS1A amino acids | Interacting amino acids of F2F3 | Remark |
|---|---|---|
| F103 | L72, Y88, M93, P111 | F103 contributes to both the tetramer interface and the CPSF30-binding epitope F103 interacts with F2 and F3 domains of CPSF30, may play a role in defining angle between F2 and F3 appropriately; mutation of 103 could affect an intermolecular salt bridge between R73 and D125. |
| L105 | P111, F112, M124 (NS1A-2) | L105 contributes to both the tetramer interface and the CPSF30-binding epitope Adjacent to F103 and also interacting at the tetramer interface with a $2^{nd}$ NS1A molecule. |
| M106 | N107 | M106 contributes to both the tetramer interface and the CPSF30-binding epitope. M106I mutation would effect the positioning of N107 (of F2F3) and/or Q121 (NS1A same molecule) involved in F2F3-NS1A H-bonds. |
| K110 | K110 | K110 contributes to the CPSF30-binding epitope. K110 has H-bond with the main-chain carbonyl of K101 of F2F3. |
| I117 | F102 | I117 contributes to the CPSF30-binding epitope. Part of the hydrophobic pocket that binds F3 |

TABLE 1-continued

Tetramerization, RNA binding and CPSF30 binding epitopes of NS1A.

| NS1A amino acids | Interacting amino acids of F2F3 | Remark |
|---|---|---|
| I119 | F98, F102 | I119 contributes to the CPSF30-binding epitope. Part of the hydrophobic pocket that binds F3 |
| Q121 | S105, S106 | Q121 contributes to the CPSF30-binding epitope. H-bond with amino group of S106 and Oγ of 105 (both from CPSF30) |
| D125 | R73 | D125 contributes to the CPSF30-binding epitope. Salt bridge with R73 (of CPSF30) |
| L144 | No inter-molecular interaction | L144 is buried into the hydrophobic core of NS1A that probably defines the fold of the protein. A mutation of L144 may alter the shape of NS1A, resulting in reduced CPSF30 and/or dsRNA binding activities |
| V180 | Y97, K101, F102 | V180 contributes to the CPSF30-binding epitope. Part of the F3-binding pocket. |
| G183 | Y97 | G183 contributes to the CPSF30-binding epitope. Part of a helix that forms a wall of the F3-binding pocket. A side-chain may affect (enhance or disrupt) the binding of F3. |
| G184 | Y97, F98 | G184 contributes to the CPSF30-binding epitope. Part of a helix that forms a wall of the F3-binding pocket. Positioned between Y97 and F98 side chains. A mutation of G184 would alter the shape of the pocket and can severely affect the binding of F3. |
| W187 | C96, Y97, F98, F112 | W187 contributes to the CPSF30-binding epitope. Participates in the pocket formation. |

Recently, the crystal structure of the NS1A effector domain (residues 79 to 205) of the influenza A/PR8/34 (PR8) virus strain was reported (Bornholdt and Prasad, 2006). This PR8 influenza strain is adapted for passage in mouse, presumably as a result of mouse adaptation, the PR8 NS gene attenuates virus growth in mammalian cells in tissue culture (Ozaki et al, 2004). The PR8 NS1A protein does not bind F2F3 because it lacks the consensus human sequence at positions 106 (I instead of M) and 103 (S instead of F) (Macken et al, 2001), therefore we can determine if the attenuation of growth in mammalian cells is caused primarily by the changed amino acids at positions 106 and 103 in the PR8 NS1A protein (data not shown). The absence of a CPSF30 binding epitope in the PR8 NS1A protein presumably resulted from the large number of passages in mice that have adapted the virus for replication in mice. Consequently, the 3D structure of effector domain of the PR8 NS1A protein (Bornholdt and Prasad, 2006) is not suitable for structure-based drug discovery efforts. In addition, its structure may differ from that of a NS1A protein containing a functional CPSF30 binding epitope. Indeed, the 3D structures of the Udorn effector domain monomers in our complex are similar to, but not identical with, the structure of the monomers of the PR8 NS1A effector domain structure (FIG. 6). The PR8 NS1A structure does not have a F2F3-binding epitope like that observed in the 3D structure of the Udorn NS1A structure described herein. In particular, the PR8 NS1A structures lack the hydrophobic pocket that binds F2F3 in the NS1A:F2F3 complex. Moreover, the dimeric interface in crystal structure of the PR8 NS1A effector domain has an intermolecular beta-sheet interaction (FIG. 7) that is completely different from the interface in the crystal structure of the Udorn NS1A effector domain bound to F2F3. Therefore, the dimer of the effector domain of the PR8 NS1A protein is not relevant for the binding of CPSF 30 and to our proposed drug-design strategy.

Fluorescence polarization (FP) assay. Fluorescence polarization (FP) is a spectroscopic method that measures the rotational rate of a sample in solution. It applies polarized light to excite a fluorophore and measures the polarization characteristics of the emitted light (Nasir and Jolley, 1999; Roehrl et al., 2004b). If the sample tumbles slowly compared to the lifetime of the fluorescence, the emitted light retains some of the incident polarization. However, if the sample tumbles fast, the emitted light is isotropic. Therefore, the degree of anisotropy (polarization) of the fluorescent light emitted from a sample provides a measure of the fluorophore's rotational correlation time in the bound state. Given appropriate bound-state lifetimes, rotational correlation times, and changes in rotational correlation upon complex formation, FP assays can be used to measure binding affinities and to screen for binding inhibitors (Schade et al., 1996; Seethala and Menzel, 1998; Roehrl et al., 2004a).

FP with fluorescently-labeled F2F3. A FP assay of F2F3 binding by NS1A is being implemented. As mentioned above, complex formation between F2F3 and various effector domain constructs is observed in gel filtration studies (see FIG. 3), indicating a dissociation constant $K_d$ tighter than low micromolar. These data of FIG. 3 demonstrate the feasibility of implementing a FP assay for detecting NS1A:F2F3 binding. Moreover, excellent HSQC spectra and essentially complete NMR resonance assignments are available for the F2F3 construct (data not shown); these will be used to assess the native structural integrity of fluorescently-labeled CPSF30 fragments.

In one embodiment of the invention, we will generate a fluorescein (or other fluorophore)—labeled F2F3 (Fluo-F2F3) substrate for FP assay. The F2F3 sequence of human CPSF30 contains 7 Lys and 6 Cys residues, and fluorophore labeling requires careful consideration to ensure proper folding with Zn ligation by these six Cys residues. Two primary strategies will be pursued for labeling F2F3: (i) chemical synthesis with a fluorophore label and (ii) synthesis or biosynthesis of an analog suitable for specific labeling. The 61-residue F2F3 is sufficiently short to allow fluorophore labeling by solid phase peptide synthesis (for example, by a commercial supplier, such as New England Peptide, Inc. Gardner, Mass.). The crystal structure of F2F3 bound to the NS1A effector domain indicates that the N-terminal region is not involved in key binding interactions, and suggests that it may be possible to generate shorter constructs with similar binding affinities. Those constructs that show tight binding can be synthesized in 100 mg amounts and assayed for structural integrity by $^{15}$N—$^1$H HSQC NMR analysis at natural isotopic abundance using a 800 MHz NMR system with cryoprobe.

If for some reason this approach is not successful, fluorophone-labeled F2F3 will be produced by overexpression with a 'flash' peptide sequence tag (Griffin et al., 1998; Griffin et al., 2000; Abrams, 2002). When the tetra-cysteine tag [NH$_2$-Cys-Cys-Pro-Gly-Cys-Cys . . . ] is incorporated into proteins/peptides it can be specifically conjugated to a biarsenyl-fluorophore ligand (sold by Invitrogen as their Lumio-technology). The modification can even specifically label the tetra-cysteine tag in vivo (Griffin et al., 2000), and thus should not react with any of the six cysteine residues on F2F3. If even both of these approaches prove to be problematic for this tandem Zn-finger domain, alternative strategies for fluorophore labeling are available, such as the method of Ting and colleagues (Chen and Ting, 2005) that utilizes biotin ligase together with appropriate cofactors to introduce fluorescein in a short N-terminal acceptor peptide lacking any Cys residues, allowing the fluorophore to be introduced subsequent to forming the Zn fingers.

Using any of the above labeling approaches, or other possible approaches, the labeled F2F3 can then be folded with Zn ligation using the same protocol we have developed for unlabeled F2F3. In exploring each of these approaches, we will verify that the fluorophore in the N-terminal tag becomes sufficiently immobilized in the complex to provide a significant change in fluorescence anisotropy. If required, a more immobilized Cys residue within the F2F3 sequence with be introduced without interfering with Zn finger formation, using our 3D structure of the NS1A (85-215):F2F3 complex as a guide. Using one of these labeling routes, or any approach for introducing the fluorescence tag, the resulting FP assay will be validated by measuring competition with unlabeled F2F3.

Figure 5:
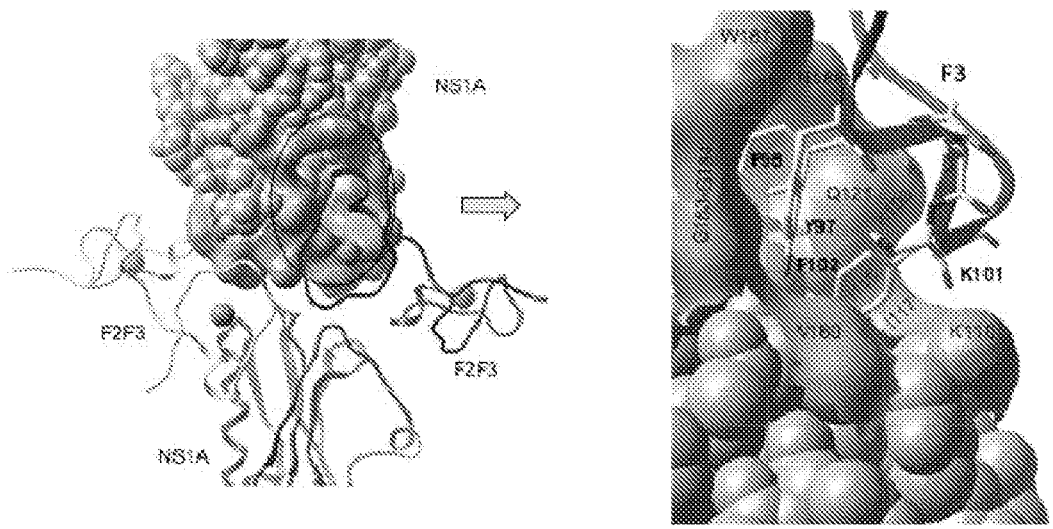
FIG. 5 shows the X-ray crystal structure for the F2F3 binding epitope on the surface of the NS1A effector domain.
Figure 6:
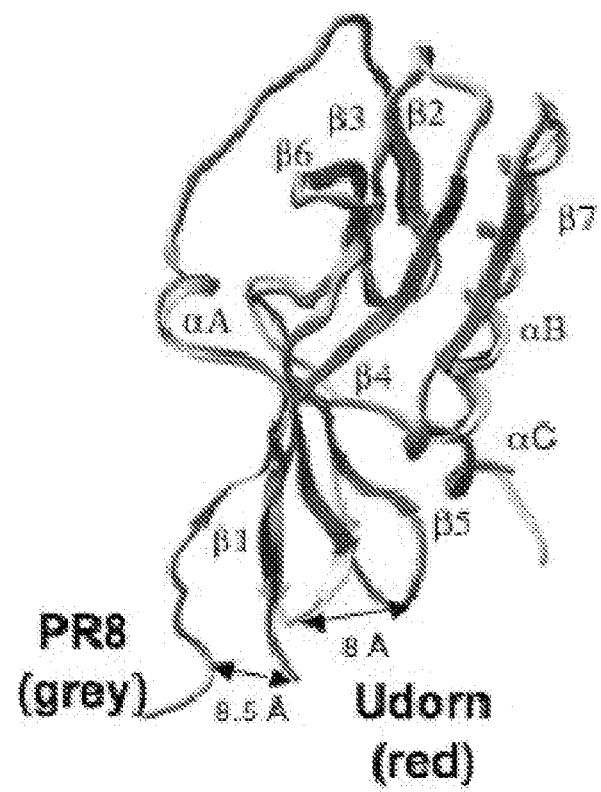
FIG. 6 is a comparison of 3D structures for Udorn and PR8 NS1A effector domains.
Figure 7:
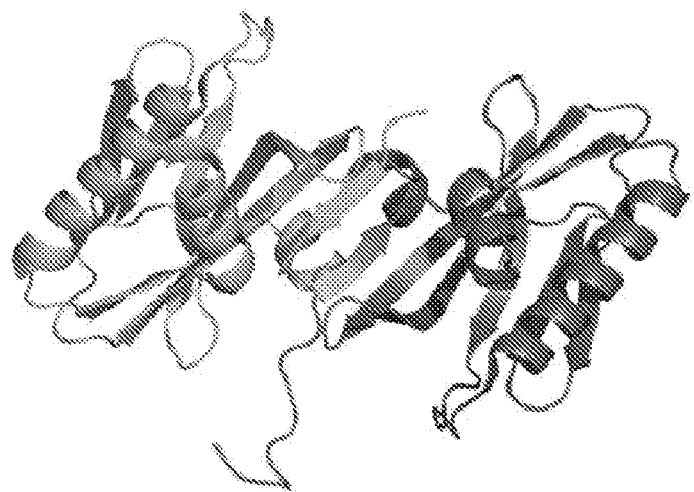
FIG. 7 shows the 3D structure and dimeric beta-sheet interface of the PR8 effector domain, which does not bind F2F3.

The crystal structure of the complex between NS1A Udorn (85-215) and the F2F3 CPSF30 reveals that most of the intermolecular interactions between NS1A and F2F3 involve the F3 Zn-finger domain (FIG. 5). Accordingly, a smaller flourescein-labeled F3 finger (Fluo-F3), with ~4 kDa molecular weight, may have preferential properties in developing a FP assay. Though the binding of the NS1A effector domain to Fluo-F3 is likely to be somewhat weaker than the binding to F2F3, the change in rotational correlation time, and thus the signal-to-noise of the FP assay, will be significantly higher using Fluo-F3 than using Fluo-F2F3. These design principles may be advantageous in development of a high throughput FP assay useful in screening for inhibitors of CPSF30 (or variants, mutants, or fragments thereof) binding to NS1A (or variants, mutants, or fragments thereof).

The crystal structure of the complex between NS1A Udorn (85-215) and the F2F3 fragment further suggests that a tandem repeat of the F2F3 fragment, connected by a short flexible linker, F2F3-F2F3, could also bind in a manner similar to the two independent F2F3 molecules, though potentially with much tighter binding affinity. Accordingly, we will generate a variety of F2F3-F2F3 constructs, as outlined below, assay their binding, and assess the oligomerization states of these complexes by gel filtration with light scattering detection. If indeed a tandem repeat F2F3-F2F3 construct can be generated with even tighter binding than F2F3 itself, it will be used in a more sensitive FP assay, capable of detecting only more tightly-binding inhibitors.

The magnitude of the change in fluorescence anisotropy, which determines the signal-to-noise of the FP assay, depends on the change in rotational correlation time of the fluorophore upon complex formation. If required to enhance this change in rotational correlation time, the relative size of the NS1A component of NS1A:CSPF30 (or fragments thereof) complexes described above can be further increased by expression as a larger fusion protein (e.g., fused to maltose binding protein), or by attachment to beads or microscopic particles using, for example, already available constructs of Tables 2, 3, and 4 with either N- or C-terminal hexHis tags, or using other affinity tags.

EXAMPLE 2

Constructs to be Used in Developing Fluorescence Polarization Assay. The crystal structure of the complex between NS1A Udorn (85-215) and the F2F3 fragment was examined to identify potential linking sites so that the C-terminus of one segment of F2F3 (or portion thereof) would have a favorable path for linking to the N-terminus of the second segment. Considerations for favorable linking geometry include the distance between termini to be linked, the path the linker would need to take, and linker composition and length. A common peptide linker composition used for connecting domains in engineered proteins is some combination of Gly and Ser residues, allowing for conformational flexibility and solubility while remaining somewhat neutral in chemical content, e.g.-Gly-Ser-, or -Gly-Ser-Gly, etc.

Constructs were designed based on the crystal structure of the influenza virus NS1A-CTD protein complex with the F2F3 fragment from the human CPSF30 protein, disclosed for this first time in this Disclosure. The expectation is that a single-chain construct of the F2F3 binding regions observed in the crystal structure would bind more tightly to the NS1A dimer than the separate domains, and might have significant antiviral activity.

The structure was examined to identify potential linking sites so that the C-terminus of one segment of F2F3 (or portion thereof) would have a favorable path for linking to the N-terminus of the second segment. Considerations for favorable linking geometry include the distance between termini to be linked, the path the linker would need to take, and linker composition and length. A common peptide linker composition used for connecting domains in engineered proteins is some combination of Gly and Ser residues, allowing for conformational flexibility and solubility while remaining somewhat neutral in chemical content, e.g.-Gly-Ser-, or -Gly-Ser-Gly, etc.

The sequence of CPSF30 F2F3 used for the specific designs is that used in the crystal structure determination, but amino acid replacements can be considered. The N-terminal portion might include a hexa-His or other tag for convenient purification; alternatively a tag might be encoded at the C-terminus of the construct. Other purification tags may be preferable to oligo-His owing to potential interference with the chelation of zinc ions by the F2 and F3 "Zn finger" segments, which is required for the integrity of the three-dimensional structure and for effective binding to NS1A. In all of these F2F3 sequences, residue Pro92 may be substituted by Ser. The constructs involving single F3 domains ("one finger") as opposed to F2F3 domains ("two fingers") are potentially valuable as minimal/miniature versions because the interaction between separate F2F3 chains in the dimer (chains F2F3-A and F2F3-B) is mediated entirely by residues in F3 and does not involve any residues from F2. The F3 domain itself, or variants, could be used as an antiviral drug.

Relatively few of the residues in F2 make important interactions with the NS1A protein in the dimer of dimers; notable exceptions are Leu72 and Arg73, whose side chains interact extensively with NS1A. The Leu72 and Arg73 interactions could be maintained by a strategic linkage of a Leu-Arg or Arg-Leu peptide to Thr91 (proposed N-terminus of the F3 domain construct). L72-T91 distance is 14.2 Å; R73-T91 distance is 17.6 Å. Possible extensions to the one-finger F3 domain construct would be Leu-Arg-GSGSG-F3 or Arg-Leu-GSGSG-F3 (see proposed constructs 5a and 5b).

F2F3 sequence (numbered as in human CPSF30 protein):

```
                                          (SEQ ID NO.: 2)
   61          71          81          91
M SGEKTVVCKH WLRGLCKKGD QCEFLHEYDM TKMPECYFYS 101         111
KFGECSNKEC PFLHIDPESK I
```

Construct 1. F3-F3: Single F3-linker-F3 construct (tandem F3 construct)(abbreviated: (91-116)-linker(11+)-(91-116)). Distance from F2F3-A Asp116 Ca to F2F3-B Thr91 Ca is 33.3 Å; linker can be 10+ flexible amino acids;

```
                                          (SEQ ID NO.: 3)
11: -GSGSGSGSGSG- also written as -(GS)₅G-;
```

```
                                          (SEQ ID NO.: 4)
13: -GSGSGSGSGSGSG- also written as -(GS)₆G-;
```

```
                                          (SEQ ID NO.: 5)
   91          101         111    linker
TKMPECYFYS KFGECSNKEC PFLHID - (GS)ₙG -

91          101         111 116
TKMPECYFYS KFGECSNKEC PFLHID
```

C-terminal residue of tandem construct can be D116 or any extension up to I121; crystal structure extends only to P117 in one copy and E118 in the other. Both N- and C-termini can have extensions including hexaHis and other tags for convenient purification as discussed in the text.

Construct 2. F2F3-F3: Same as previous construct except that the N-terminal portion of the construct encompasses entire F2F3 segment (abbreviated) (60-116)-linker(11+)-(91-116)

```
                                          (SEQ ID NO.: 6)
   61          71          81          91
M SGEKTVVCKH WLRGLCKKGD QCEFLHEYDM TKMPECYFYS 101         111    linker    91
KFGECSNKEC PFLHID - (GS)ₙG - TKMPECYFYS 101         111 116
KFGECSNKEC PFLHID
```

Construct 3. F2F3-F2F3: F2F3-linker-F2F3 construct (tandem F2F3 construct)(abbreviated: (60-116)-linker(15+)-(62-116)). Distance from F2F3-A Asp116 Ca to F2F3-B Gly62 Ca is 51.1 Å; linker should be 14+ flexible amino acids.

```
                                          (SEQ ID NO.: 7)
15: -GSGSGSGSGSGSGSG- also written as -(GS)₇G-;
```

```
                                          (SEQ ID NO.: 8)
17: -GSGSGSGSGSGSGSGSG- also written as -(GS)₈G-;
```

```
                                          (SEQ ID NO.: 9)
   61      71          81          91          101
M SGEKTVVCKH WLRGLCKKGD QCEFLHEYDM TKMPECYFYS 111          linker    62          71
KFGECSNKEC PFLHID - (GS)ₙG - GEKTVVCKH WLRGLCKKGD
```

```
   81          91          101         111
QCEFLHEYDM TKMPECYFYS KFGECSNKEC PFLHID.
```

Construct 4. F3-F2F3: F3-linker-F2F3 construct (abbreviated: (91-116)-linker(15+)-(62-116)). Distance from F2F3-A Asp116 Ca to F2F3-B Gly62 Ca is 51.1 Å; linker should be 14+ flexible amino acids.

```
                                          (SEQ ID NO.: 10)
   91      101         111 116  linker   62
TKMPECYFYS KFGECSNKEC PFLHID - (GS)ₙG - GEKTVVCKH 71          81          91          101         111
WLRGLCKKGD QCEFLHEYDM TKMPECYFYS KFGECSNKEC PFLHID
```

Construct 5. XF3-F3: Extended F3-linker-F3 construct. Linker 1 will link a Leu-Arg or Arg-Leu dipeptide to the one-finger F3 domain in a mode to incorporate the important L72 and R73 side-chain interactions from F2 that are otherwise missing. Linker 2 can be 10+ flexible amino acids:

Construct 5a (abbreviated: Leu-Arg-linker(5+)-(91-116)-linker(11+)-(91-116)):

```
                                          (SEQ ID NO.: 11)
72 73  linker 1  91          101         111 116
Leu-Arg - GSGSG - TKMPECYFYS KFGECSNKEC PFLHID - linker 2  91          101         111 116
(GS)ₙG - TKMPECYFYS KFGECSNKEC PFLHID
```

Construct 5b (abbreviated: Arg-Leu-linker(5+)-(91-116)-linker(11+)-(91-116)):

```
                                          (SEQ ID NO.: 12)
73 72  linker 1  91          101         111 116
Arg-Leu - GSGSG - TKMPECYFYS KFGECSNKEC PFLHID - linker 2  91          101         111 116
(GS)ₙG - TKMPECYFYS KFGECSNKEC PFLHID
```

Each of the constructs 1-5b above, and variants thereof, will inhibit CPSF30 binding by NS1A, and can potentially be used as lead compounds for drug development and/or as antiviral drugs useful in preventing or treating influenza A infection in humans, poultry (e.g. chicken), and other animals.

Structure-based Lead Optimization using X-ray Crystallography and NMR. The sample preparation and structural characterization of NS1A effector domains from multiple influenza strains, allow the use of both NMR and X-ray crystallography in hit validation, lead compound optimization, and drug discovery.

Crystallography for lead optimization. X-ray analysis has historically been very important to structure-based inhibitor design. Compounds identified as inhibitor "hits" by kinetic assays can be used to form complexes with the target protein. X-ray analysis will reveal the mode of inhibitor binding and act as a basis for further inhibitor design. Crystale•inhibitor complexes can also be formed by soaking inhibitors into preformed crystals, or complexes may be grown by co-crystallization. The latter case may be necessary if the complex triggers conformational changes. In either case, diffraction data is collected on a rotating anode source, processed, and converted to electron density maps. The orientation and occupancy of the inhibitors will be observed and compared with binding modes predicted from virtual screening or models from earlier design cycles. In this way, inhibitors analyzed in one cycle of design will feed into subsequent rounds of structural analysis and re-design in the general process of structure-based drug design (Kuhn 2002; Scapin 2006)

Cocrystallization and Crystal soaks. Using crystallization conditions that we have already optimized for the NS1A effector domains, described above, cocrystallizations and crystal soaks can be carried out with lead compounds identified in our high throughput screening efforts. Trials will be carried out to crystallize NS1A effector domain:lead compound complexes. Diffraction data can be collected using either home or synchrotron X-ray sources and the resulting difference electron density maps and 3D structures can be used to characterize small molecule binding epitopes and bound-state conformations. These data can be used screening for lead compounds either one at a time or in high throughput format, lead compound validation, and optimization of lead compounds, using methods familiar to a person skilled in the art.

NMR for lead identification optimization. NMR is also a powerful method for validating intermolecular interactions, and is used extensively in commercial pharmaceutical drug discovery efforts to identify lead compounds and their protein binding sites (Shuker et al., 1996; Hajduk et al., 1997; Moore, 1999a, 1999b; Muegge et al., 1999; Moy et al., 2001; Powers, 2002; Lepre et al., 2004; Rush and Powers, 2004; Mercier et al., 2006; Petros et al., 2006). NMR chemical shift perturbations, of either the protein or the ligand, can be used for screening for small molecule lead compounds, validating initial small molecule hits identified with htp or virtual screening assays, locating the corresponding binding site in the 3D protein structure, and to guide rational lead optimization. NMR methods uniquely complement crystallography studies. Strengths of NMR analysis methods include (i) the ability to detect even weak ($K_d$ up to ~500 micromolar) binding interactions, (ii) compatibility with systems that undergo structural changes upon ligand binding which may not be accommodated by a crystalline lattice, (iii) the ability to adjust solvent conditions over a wide range, and (iv) high sensitivity and very low sample requirements.

Using NS1A effector domain constructs that have already been shown to provide high quality HSQC spectra (e.g., FIG. 2), NMR chemical shift perturbation can be used to validate initial small molecule hits identified with high-throughput (htp) or virtual screening assays, locating the corresponding binding site in the 3D protein structure, and for rational lead optimization. Hits identified in htp FP assays will be characterized by assessing perturbations in HSQC spectra for which resonance assignments will be available, and interpreting these effects on the available 3D structures of NS1 effector domains. Some methods suitable for lead compound screening, identification, and optimization envisioned for use with our invention are summarized in C.A. Lepre, J. M, Moore, and J. W. Peng, Theory and Applications of NMR-based Screening in Pharmaceutical Research (Chem. Rev. 104, 3641-3675 (2004)), which is incorporated herein by reference. The NMR infrastructure required for such work are available at most large research institutions, including by not limited to Rutgers University, and include 5 mm 600 and 800 MHz NMR cryoprobe systems, as well as a 1 mm 600 MHz NMR equipped with an automated sample changer. The cryoprobes enable recording of high-quality HSQC data using 150 microliter samples at protein concentrations as low as 10 micromolar, and the 1 mm NMR probe provides high quality HSQC data on 7 microliter samples at 100 micromolar concentrations. Such NMR technologies allow NMR screening for lead compound optimization with as little as ~500 nanomoles of each sample. Where appropriate, the 3D structures of tightly bound small molecule lead compounds may also be determined by NMR methods if they cannot be solved by crystallographic methods. These data will be used in redesign and lead optimization as outlined for crystallographic data above.

Expressed soluble constructs of NS1A outlined in Tables 2, 3 and 4, or their variants, can also be used to screen for small molecule lead compounds using NMR detection of resonances of the small molecule, using limits described by (but not limited to) C. A. Lepre, J. M, Moore, and J. W. Peng, Theory and Applications of NMR-based Screening in Pharmaceutical Research (Chem. Rev. 104, 3641-3675 (2004)).

Where appropriate, the 3D structures of tightly bound small molecule lead compounds may also be determined by NMR methods if they cannot be solved by crystallographic methods. These data will be used in redesign and lead optimization using synthetic chemistry, as outlined for crystallographic data above.

Antiviral assays. Having identified inhibitors of the interaction between NS1A and CPSF30, the inhibitors would be tested for their ability to inhibit influenza A virus replication in tissue culture studies. Plaque reduction assays in MDCK cells will be used to assay compounds for their ability to inhibit influenza A virus replication (Twu et al., 2006). Monolayers of MDCK cells will be infected with approximately 100 plaque-forming units (PFU) of influenza A/Udorn/72 virus, and after virus adsorption the cells will be overlaid with agar containing a concentration of a compound ranging from 0.001 micrograms/ml to 10 micrograms/ml. Plaques will be counted in duplicate plates and compared to the number of plaques in controls not exposed to the chemical. In parallel cytotoxicity evaluations of lead compounds would be carried out on MDCK cells using the Roche reagent WST-1 (Berridge et al, 2005). The rate of WST-1 cleavage by mitochondrial dehydrogenases, yielding a product with absorbance at 450 nm, correlates with the number of viable cells. These assays will be carried out in 96-well tissue culture plates, and cell viability will be assayed by determining absorbance at 450 nm using an ELISA plate reader. Once the most promising lead compounds with low cytotoxicity in both MDCK and human (A549) cells have been identified, we will determine the effect of several concentrations of the compounds on the rate and extent of virus replication during multiple-cycle growth in MDCK cells. The compounds with the greatest inhibitory activity at the lowest concentrations will be used for subsequent studies in a suitable animal model (ferrets).

Applications of NS1A:CPSF30 Inhibitors. These inhibitors can be developed into antiviral drugs that will be effective in the control of influenza virus epidemics and pandemics in humans. Because there is the potential for such epidemics to be man-made, i.e., using influenza A virus as a bioterrorist weapon, such antivirals would also be crucial in this situation. Influenza antiviral drugs will also be important for the control of influenza A infections in commercial poultry stocks, such as chickens.

TABLE 2 pET-based vectors for NS1A proteins and fragments from various flu strains.

|  | 1918 | HK97 | VN04 | Udorn |
|---|---|---|---|---|
| Full-length | N-His and C-His | N-His and C-His | N-His and C-His | N-His and C-His |
| 1-215 | N-His and C-His | N-His and C-His | N-His and C-His | N-His and C-His |
| 73-215 | N-His and C-His | N-His and C-His | N-His and C-His | N-His and C-His |
| 85-215 | N-His and C-His | N-His and C-His | N-His and C-His | N-His and C-His |
| 91-215 | C-His | Not attempted | C-His | C-His |
| 1-211 | N-His and C-His | N-His and C-His | N-His and C-His | N-His and C-His |
| 85-211 | N-His and C-His | N-His and C-His | N-His and C-His | N-His and C-His |
| 73-211 | N-His and C-His | N-His and C-His | N-His and C-His | N-His and C-His |
| 91-211 | C-His | Not attempted | Not attempted | Not attempted |
| 85-204 | C-His | C-His | C-His | C-His |
| 91-204 | C-His | Not attempted | C-His | C-His |

TABLE 3

N-terminal His tag NS1 Expression/Solubility results for NS1A proteins and fragments from various flu strains

|  | 1918 | HK97 | VN04 | Udorn |
|---|---|---|---|---|
| FL | yes/low | yes/low | no/na | yes/low |
| 1-215 | yes/low | yes/low | yes/no | yes/low |
| 73-215 | yes/no | yes/med | yes/no | yes/low |
| 85-215 | yes/low | yes/low | yes/low | yes/med |
| 1-211 | yes/no | yes/low | yes/no | yes/low |
| 85-211 | yes/low | yes/no | yes/med | yes/med |
| 73-211 | yes/low | yes/no | yes/med | yes/low |

TABLE 4

C-terminal His tag NS1 Expression/Solubility results for NS1A proteins and fragments from various flu strains

|  | 1918 | HK97 | VN04 | Udorn |
|---|---|---|---|---|
| FL | yes/low | yes/no | no/na | yes/low |
| 1-215 | yes/no | yes/medium | yes/no | yes/no |
| 73-215 | na | na | yes/no | yes/low |
| 85-215 | yes/medium | yes/good | yes/low | yes/low |
| 91-215 | yes/low | yes/low | na | yes/low |
| 1-211 | no/na | na | yes/no | na |
| 85-211 | yes/no | yes/no | yes/low | yes/no |
| 73-211 | na | yes/no | yes/good | yes/no |
| 91-211 | yes/no | na | na | na |
| 85-204 | yes/low | yes/low | yes/low | yes/low |
| 91-204 | yes/no | yes/no | na | yes/no |

Creating Attenuated Influenza Virus Strains Suitable for Avian and Human Influenza Vaccine Development. The structural information disclosed here can be combined with site-directed mutagenesis data for NS1A to engineer attenuated influenza A virus strains suitable for use as live attenuated vaccines in humans and livestock. Multiple, weakly attenuating mutations will be created in the CPSF30 and dsRNA-binding epitopes to generate NS1 proteins with reduced binding affinity in vitro. The effects of these mutations on the structural integrity of NS1A variants can be assessed with HSQC NMR data and/or crystallization and X-ray crystallography. These data will then be used to engineer viral strains of influenza A with various degrees of attenuation. These viral strains will be engineered to contain multiple base changes to minimize the potential of the virus to revert to virulence. Such influenza A viruses would be attenuated in normal cells, and in humans and animals, but would not be attenuated in cells lacking interferon genes (e.g. cell culture Vero cells), thereby enabling the production of large amounts of these attenuated viruses suitable for use as a live virus vaccine.

Methods for development of attenuated flu vaccines are described in U.S. Provisional Patent Application Ser. No. 60/737,742, "Novel Compositions and Vaccines Against Influenza and Influenza B Infections,", and PTC Patent Application Filed Nov. 17, 2006 "Novel Compositions and Vaccines Against Influenza and Influenza B Infections," relevant portions and tables incorporated herein by reference, relevant portions incorporated herein by reference.

A person of ordinary skill in the art will understand that because of the degeneracy of the genetic code, a large number of nucleic acid sequences can be generated in accordance with this invention. The production of the viruses of the instant invention (or the respective recombinant NS1A protein or respective NS1B protein comprising said amino acid sequences) can be achieved by recombinant DNA technology. Nucleic acid sequences encoding the amino acid sequences of the instant invention can be produced using methods well known in the art, including, for example, chemical synthesis, PCR and site-directed mutagenesis.

The instant invention provides recombinant influenza A virus comprising the amino acid sequences which are at least 70% identical but less than 100% identical either to dsRNA binding domains of NS1A. These viruses may be generated, for example, by reverse genetic system, whereby influenza virus can be generated by transfection of multiple DNAs without a helper virus. This technique was described in Fodor et al., 1999. Essentially, in that study the technique involved transfecting into a host cell a combination of plasmids containing cDNAs for the viral RNA segments (including NS1 proteins), proteins of viral RNA dependent polymerase complex (PB1, PB2, and PA), and nucleoprotein. Further, it is possible to transfect host cells (such as, for example 293 cells or Vero cells) with a plasmid encoding a recombinant NS1A protein (for rescuing influenza A viral phenotype) containing the appropriate amino acid sequence of the instant invention. The resulting viruses may be used for creation of vaccines, as described below In another embodiment, the virus can be propagated in suitable host, such as, for example, chicken eggs, without a need for transforming a host cell with multiple plasmids. In this embodiment, essentially, clinical isolates of human influenza virus are taken from infected patients and are reassorted in embryonated chicken eggs with laboratory-adapted master strains of high-growth donor viruses.

To prepare the recombinant NS1A viruses for different purposes (including, without limitations, the use of the virus as a vaccine or a part thereof), each of these mutations may be carried out individually on constructs of NS1A suitable for biochemical characterization, possibly including but not limited to the constructs outlined in Tables 3 and 4. Other variants of NS1A or affinity tags (e.g. FLAG tags) may also be used. These proteins may be purified and characterized with respect to structural integrity by comparing the circular dichroism and/or NMR spectrum and/or X-ray crystal structures with those of the corresponding wild-type NS1 construct. The several constructs may then be assayed for dsRNA binding as described elsewhere (Chien et al., 2004), or using other methods of assessing protein-dsRNA binding affinities commonly used for such studies, such as, for example, sedimentation equilibrium, gel electrophoresis, or gel filtration chromatography. These data will be used to assess the effect of single site mutants at these sites revealed by the structural models to be important for dsRNA recognition. Further, sets of double, triple, and quadruple mutants of residues in the CPSF30 binding epitope, tetramer interface, dsRNA binding epitope, and combinations thereof would also be generated in these NS1A constructs and assessed for structural integrity and binding activities in vitro. This experimental design will allow a person of the ordinary skill in the art to identify mutant forms of NS1A and NS1A variants with minimal structural disruption but with reduced CPSF30 and/or dsRNA binding affinity.

The invention encompasses methods of selecting viruses which have the desired phenotype, i.e., viruses which have low or no dsRNA binding activity, whether obtained from natural variants, spontaneous variants (i.e., variants which evolve during virus propagation), mutagenized natural variants, reassortants and/or genetically engineered viruses. Such viruses can be best screened in differential growth assays that compare growth in host systems which have attenuated and normal immune response to influenza A viruses. Viruses which demonstrate better growth in the hosts having the attenuated response versus the normal response are selected; preferably, viruses which grow to titers at least one log greater in the host systems with the attenuated response as compared to the host system with the normal response are selected.

The present invention also encompasses methods of growing and isolating mutated viruses having altered dsRNA binding activity in cells and cell lines which naturally exhibit an attenuated response to viral infections as compared to wild-type cells. In a particular preferred embodiment, the present invention relates to methods of growing the viruses of the instant invention in Vero cells.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Abrams, J. M. 2002. Competition and compensation: coupled to death in development and cancer. *Cell* 110: 403-6.

Acton, T. B., Gunsalus, K. C., Xiao, R., Ma, L. C., Aramini, J., Baran, M. C., Chiang, Y.-W., Climent, T., Cooper, B., Denissova, N. G., Douglas, S. M., Everett, J. K., Ho, C. K., Macapagal, D., Paranji, R. K., Shastry, R., Shih, L. Y., Swapna, G. V. T., Wilson, M., Wu, M., Gerstein, M., Inouye, M., Hunt, J. F., and Montelione, G. T. 2005. Robotic cloning and protein production platform of the Northeast Structural Genomics Consortium. *Meth. Enzymol.* 394: 210-43.

Berridge, M. V., Herst, P. M., and Tan, A. S. 2005. Tetrazolium dyes as tools in cell biology: new insights into their cellular reduction. *Biotechnol Annu Rev* 11: 127-52. Bornholdt, Z. A., and Prasad, B. V. 2006. X-ray structure of influenza virus NS1 effector domain. *Nat Struct Mol Biol* 13: 559-60.

Chen, I., and Ting, A. Y. 2005. Site-specific labeling of proteins with small molecules in live cells. *Curr Opin Biotechnol* 16: 35-40.

Chizhmakov, I. V., Geraghty, F. M., Ogden, D. C., Hayhurst, A., Antoniou, M., and Hay, A. J. 1996. Selective proton permeability and pH regulation of the influenza virus M2 channel expressed in mouse erythroleukaemia cells. *J Physiol* 494 (Pt 2): 329-36.

Cox, N. J., and Subbarao, K. 1999. Influenza. *Lancet* 354: 1277-82.

Crescenzo-Chaigne, B., van der Werf, S., and Naffakh, N. 2002. Differential effect of nucleotide substitutions in the 3' arm of the influenza A virus vRNA promoter on transcription/replication by avian and human polymerase complexes is related to the nature of PB2 amino acid 627. *Virology* 303: 240-52.

de Jong, M. D., Tran, T. T., Truong, H. K., Vo, M. H., Smith, G. J., Nguyen, V. C., Bach, V. C., Phan, T. Q., Do, Q. H., Guan, Y., Peiris, J. S., Tran, T. H., and Farrar, J. 2005. Oseltamivir resistance during treatment of influenza A ($H_5N_1$) infection. *N Engl J Med* 353: 2667-72.

Ferguson, N. M., Cummings, D. A., Cauchemez, S., Fraser, C., Riley, S., Meeyai, A., Iamsirithaworn, S., and Burke, D. S. 2005. Strategies for containing an emerging influenza pandemic in Southeast Asia. *Nature* 437: 209-14.

Ferguson, N. M., Cummings, D. A., Fraser, C., Cajka, J. C., Cooley, P. C., and Burke, D. S. 2006. Strategies for mitigating an influenza pandemic. *Nature* 442: 448-52.

Geiss, G. K., Salvatore, M., Tumpey, T. M., Carter, V. S., Wang, X., Basler, C. F., Taubenberger, J. K., Bumgarner, R. E., Palese, P., Katze, M. G., and Garcia-Sastre, A. 2002. Cellular transcriptional profiling in influenza A virus-infected lung epithelial cells: the role of the nonstructural NS1 protein in the evasion of the host innate defense and its potential contribution to pandemic influenza. *Proc Natl Acad Sci USA* 99: 10736-41.

Germann, T. C., Kadau, K., Longini, I. M., Jr., and Macken, C. A. 2006. Mitigation strategies for pandemic influenza in the United States. *Proc Natl Acad Sci USA* 103: 5935-40.

Griffin, B. A., Adams, S. R., Jones, J., and Tsien, R. Y. 2000. Fluorescent labeling of recombinant proteins in living cells with FlAsH. *Methods Enzymol* 327: 565-78.

Griffin, B. A., Adams, S. R., and Tsien, R. Y. 1998. Specific covalent labeling of recombinant protein molecules inside live cells. *Science* 281: 269-72.

Gubareva, L. V., Penn, C. R., and Webster, R. G. 1995. Inhibition of replication of avian influenza viruses by the neuraminidase inhibitor 4-guanidino-2,4-dideoxy-2,3-dehydro-N-acetylneuraminic acid. *Virology* 212: 323-30.

Hajduk, P. J., Dinges, J., Miknis, G. F., Merlock, M., Middleton, T., Kempf, D. J., Egan, D. A., Walter, K. A., Robins, T. S., Shuker, S. B., Holzman, T. F., and Fesik, S. W. 1997. NMR-based discovery of lead inhibitors that block DNA binding of the human papillomavirus E2 protein. *J Med Chem* 40: 3144-50.

Hatta, M., Gao, P., Halfmann, P., and Kawaoka, Y. 2001. Molecular basis for high virulence of Hong Kong H5N1 influenza A viruses. *Science* 293: 1840-2.

Hendrickson, W. A. 1991. Determination of macromolecular structures from anomalous diffraction of synchrotron radiation. *Science* 254: 51-8.

Horimoto, T., and Kawaoka, Y. 2005. Influenza: Lessons from past pandemics, warnings from current incidents. *Nature Revs. Microbiol.* 3: 591.

Kim, C. U., Lew, W., Williams, M. A., Liu, H., Zhang, L., Swaminathan, S., Bischofberger, N., Chen, M. S., Mendel, D. B., Tai, C. Y., Layer, W. G., and Stevens, R. C. 1997. Influenza neuraminidase inhibitors possessing a novel hydrophobic interaction in the enzyme active site: design, synthesis, and structural analysis of carbocyclic sialic acid analogues with potent anti-influenza activity. *J Am Chem Soc* 119: 681-90.

Kim, M. J., Latham, A. G., and Krug, R. M. 2002. Human influenza viruses activate an interferon-independent transcription of cellular antiviral genes: outcome with influenza A virus is unique. *Proc Natl Acad Sci USA* 99: 10096-101.

Krug, R. M., Yuan, W., Noah, D. L., and Latham, A. G. 2003. Intracellular warfare between human influenza viruses and human cells: the roles of the viral NS1 protein. *Virology* 309: 181-9.

Lamb, R. A., and Krug, R. M. 2001. Orthomyxoviridae: the viruses and their replication. 1487-531 In: Fields Virology, vol. 1, eds. D. M. Knipe and P. M. Howley, Lippincott, Williams, and Wilkins, Philadelphia.

Le, Q. M., Kiso, M., Someya, K., Sakai, Y. T., Nguyen, T. H., Nguyen, K. H., Pham, N. D., Ngyen, H. H., Yamada, S., Muramoto, Y., Horimoto, T., Takada, A., Goto, H., Suzuki, T., Suzuki, Y., and Y., K. 2005. Avian flu: isolation of drug-resistant H5N1 virus. *Nature* 437: 1108.

Lepre, C. A., Moore, J. M., and Peng, J. W. 2004. Theory and applications of NMR-based screening in pharmaceutical research. *Chem Rev* 104: 3641-76.

Li, Y., Chen, Z. Y., Wang, W., Baker, C. C., and Krug, R. M. 2001. The 3'-end-processing factor CPSF is required for the splicing of single-intron pre-mRNAs in vivo. *Rna* 7: 920-31.

Longini, I. M., Jr., Nizam, A., Xu, S., Ungchusak, K., Hanshaoworakul, W., Cummings, D. A., and Halloran, M. E. 2005. Containing pandemic influenza at the source. *Science* 309: 1083-7.

Luft, J. R., Collins, R. J., Fehrman, N. A., Lauricella, A. M., Veatch, C. K., and DeTitta, G. T. 2003. A deliberate approach to screening for initial crystallization conditions of biological macromolecules. *J Struct Biol* 142: 170-9.

Macken, C., Lu, H., Goodman, J., and Boykin, L. 2001. The value of a database in surveillance and vaccine selection. 103-06 In: Options for the control of influenza IV, eds. N.C.A.W.H. A. D. M. E. Osterhaus, N. Cox and A. W. Hampson Elsevier Science, Amsterdam.

Maines, T. R., Chen, L. M., Matsuoka, Y., Chen, H., Rowe, T., Ortin, J., Falcon, A., Nguyen, T. H., Mai le, Q., Sedyaningsih, E. R., Harun, S., Tumpey, T. M., Donis, R. O., Cox, N. J., Subbarao, K., and Katz, J. M. 2006. Lack of transmission of H5N1 avian-human reassortant influenza viruses in a ferret model. *Proc Natl Acad Sci USA* 103: 12121-6.

Mendel, D. B., Tai, C. Y., Escarpe, P. A., Li, W., Sidwell, R. W., Huffman, J. H., Sweet, C., Jakeman, K. J., Merson, J., Lacy, S. A., Lew, W., Williams, M. A., Zhang, L., Chen, M. S., Bischofberger, N., and Kim, C. U. 1998. Oral administration of a prodrug of the influenza virus neuraminidase inhibitor GS 4071 protects mice and ferrets against influenza infection. *Antimicrob Agents Chemother* 42: 640-6.

Mercier, K. A., Germer, K., and Powers, R. 2006. Design and characterization of a functional library for NMR screening against novel protein targets. *Comb Chem High Throughput Screen* 9: 515-34.

Montelione, G. T., Rios, C. B., Swapna, G. V. T., and Zimmerman, D. E. 1999. NMR pulse sequences and computational approaches for automated analysis of sequence-specific backbone resonance assignments of proteins. 81-130 In: Biological Magnetic Resonance Vol 17, vol. 17, eds. N. R. Krishna and L. J. Berliner, Kluwer Academic/Plenum publishers, New York.

Moore, J. M. 1999a. NMR screening in drug discovery. *Curr Opin Biotechnol* 10: 54-8.

Moore, J. M. 1999b. NMR techniques for characterization of ligand binding: utility for lead generation and optimization in drug discovery. *Biopolymers* 51: 221-43.

Moy, F. J., Haraki, K., Mobilio, D., Walker, G., Powers, R., Tabei, K., Tong, H., and Siegel, M. M. 2001. MS/NMR: a structure-based approach for discovering protein ligands and for drug design by coupling size exclusion chromatography, mass spectrometry, and nuclear magnetic resonance spectroscopy. *Anal Chem* 73: 571-81.

Muegge, I., Martin, Y. C., Hajduk, P. J., and Fesik, S. W. 1999. Evaluation of PMF scoring in docking weak ligands to the FK506 binding protein. *J Med Chem* 42: 2498-503.

Nasir, M. S., and Jolley, M. E. 1999. Fluorescence polarization: an analytical tool for immunoassay and drug discovery. *Comb. Chem. High Throughput Screen* 2: 177-90.

Nemeroff, M., Barabino, S. M. L., Keller, W., and Krug, R. M. 1998. Influenza virus NS1 protein interacts with the 30 kD subunit of cleavage and specificity factor and inhibits 3' end formation of cellular pre-mRNAs. *Mol. Cell.* 1: 991-1000.

Noah, D. L., and Krug, R. M. 2005. Influenza virus virulence and its molecular determinants. *Adv Virus Res* 65: 121-45.

Noah, D. L., Twu, K. Y., and Krug, R. M. 2003. Cellular antiviral responses against influenza A virus are countered at the posttranscriptional level by the viral NS1A protein via its binding to a cellular protein required for the 3' end processing of cellular pre-mRNAS. *Virology* 307: 386-95.

Ozaki, H., Govorkova, E. A., Li, C., Xiong, X., Webster, R. G. and Webby, R. J. 2004. Generation of high-yielding influenza A viruses in African green monkey kidney (Vero) cells by reverse genetics. *J. Virol.* 78: 1851-7.

Petros, A. M., Dinges, J., Augeri, D. J., Baumeister, S. A., Betebenner, D. A., Bures, M. G., Elmore, S. W., Hajduk, P. J., Joseph, M. K., Landis, S. K., Nettesheim, D. G., Rosenberg, S. H., Shen, W., Thomas, S., Wang, X., Zanze, I., Zhang, H., and Fesik, S. W. 2006. Discovery of a potent inhibitor of the antiapoptotic protein Bcl-xL from NMR and parallel synthesis. *J Med Chem* 49: 656-63.

Pinto, L. H., Holsinger, L. J., and Lamb, R. A. 1992. Influenza virus M2 protein has ion channel activity. *Cell* 69: 517-28.

Powers, R. 2002. Applications of NMR to structure-based drug design in structural genomics. *J Struct Funct Genomics* 2: 113-23.

Prevention. 2005. Background on Influenza. http://www.cdc.gov/flu/background/professionals/background.

Puthavathana, P., Auewarakul, P., Charoenying, P. C., Sangsiriwut, K., Pooruk, P., Boonnak, K., Khanyok, R., Thawachsupa, P., Kijphati, R., and Sawanpanyalert, P. 2005. Molecular characterization of the complete genome of human influenza H5N1 virus isolates from Thailand. *J. Gen. Virol.* 86: 423-33.

Reid, A. H., Taubenberger, J. K., and Fanning, T. G. 2001. The 1918 Spanish influenza: integrating history and biology. *Microbiol. Infect.* 3: 81-7.

Reid, A. H., Taubenberger, J. K., and Fanning, T. G. 2004. Evidence of an absence: the genetic origins of the 1918 pandemic influenza virus. *Nat Rev Microbiol* 2: 909-14.

Roehrl, M. H. A., Wang, J. Y., and Wagner, G. 2004a. Disovery of small-molecule inhibitors of the NFAT-calcineurin interaction by competitive high-throughput fluorescence polarization screening. *Biochemistry* 43: 16067-75.

Roehrl, M. H. A., Wang, J. Y., and Wagner, G. 2004b. A general framework for development and data analysis of competitive high-throughput screens for small-molecule inhibitors of protein-protein interactions by fluorescence polarization. *Biochemistry* 43: 16056-66.

Rush, T. S., 3rd, and Powers, R. 2004. The application of x-ray, NMR, and molecular modeling in the design of MMP inhibitors. *Curr Top Med Chem* 4: 1311-27.

Ryan, D. M., Ticehurst, J., Dempsey, M. H., and Penn, C. R. 1994. Inhibition of influenza virus replication in mice by GG167 (4-guanidino-2,4-dideoxy-2,3-dehydro-N-acetylneuraminic acid) is consistent with extracellular activity of viral neuraminidase (sialidase). *Antimicrob Agents Chemother* 38: 2270-5.

Schade, S. Z., Jolley, M. E., J., S. B., and Simonson, L. G. 1996. BODIPY-alpha-casein, a pH-independent protein substrate for protease assays using fluorescence polarization. *Anal Biochem.* 24: 31-37.

Seethala, R., and Menzel, R. 1998. A fluorescence polarization competition immunoassay for tyrosine kinases. *Anal. Biochem* 255: 257-62.

Seth, R. B., Sun, L., and Chen, Z. J. 2006. Antiviral innate immunity pathways. *Cell Res* 16: 141-7.

Shimizu, K., Iguchi, A., Gomyou, R., and Ono, Y. 1999. Influenza virus inhibits cleavage of the HSP70 pre-mRNAs at the polyadenylation site. *Virology* 254: 213-9.

Shinya, K., Hamm, S., Hatta, M., Ito, H., Ito, T., and Kawaoka, Y. 2004. PB2 amino acid at position 627 affects replicative efficiency, but not cell tropism, of Hong Kong H5N1 influenza A viruses in mice. *Virology* 320: 258-66.

Shuker, S. B., Hajduk, P. J., Meadows, R. P., and Fesik, S. W. 1996. Discovering high-affinity ligands for proteins: SAR by NMR. *Science* 274: 1531-4.

Siren, J., Imaizumi, T., Sarkar, D., Pietila, T., Noah, D. L., Lin, R., Hiscott, J., Krug, R. M., Fisher, P. B., Julkunen, I., and Matikainen, S. 2006. Retinoic acid inducible gene-I and mda-5 are involved in influenza A virus-induced expression of antiviral cytokines. *Microbes Infect* 8: 2013-20.

Sumpter, R., Jr., Loo, Y. M., Foy, E., Li, K., Yoneyama, M., Fujita, T., Lemon, S. M., and Gale, M., Jr. 2005. Regulating intracellular antiviral defense and permissiveness to hepatitis C virus RNA replication through a cellular RNA helicase, RIG-1. *J Virol* 79: 2689-99.

Suzuki, H., Saito, R., Masuda, H., Oshitani, H., Sato, M., and Sato, I. 2003. Emergence of amantadine-resistant influenza A viruses: epidemiological study. *J Infect Chemother* 9: 195-200.

Taubenberger, J. K., Reid, A. H., Lourens, R. M., Wang, R., Jin, G., and Fanning, T. G. 2005. Characterization of the 1918 influenza virus polymerase genes. *Nature* 437: 889-93.

Thompson, J. D., Higgins, D. G. and Gibson, T. J. (1994) CLUSTAL W: improving the sensitivity of progressive multiple sequence alignment through sequence weighting, position specific gap penalties and weight matrix choice. Nucleic Acids Res. 22:4673-80.

Twu, K. Y., Noah, D. L., Rao, P., Kuo, R. L., and Krug, R. M. 2006. The CPSF30 binding site on the NS1A protein of influenza A virus is a potential antiviral target. *J Virol* 80: 3957-65.

von Itzstein, M., Wu, W. Y., Kok, G. B., Pegg, M. S., Dyason, J. C., Jin, B., Van Phan, T., Smythe, M. L., White, H. F., Oliver, S. W., and et al. 1993. Rational design of potent sialidase-based inhibitors of influenza virus replication. *Nature* 363: 418-23.

Wang, C., Takeuchi, K., Pinto, L. H., and Lamb, R. A. 1993. Ion channel activity of influenza A virus M2 protein: characterization of the amantadine block. *J Virol* 67: 5585-94.

WHO. 2006. Pandemic influenza.

Woods, J. M., Bethell, R. C., Coates, J. A., Healy, N., Hiscox, S. A., Pearson, B. A., Ryan, D. M., Ticehurst, J., Tilling, J., Walcott, S. M., and et al. 1993. 4-Guanidino-2,4-dideoxy-2,3-dehydro-N-acetylneuraminic acid is a highly effective inhibitor both of the sialidase (neuraminidase) and of growth of a wide range of influenza A and B viruses in vitro. *Antimicrob Agents Chemother* 37: 1473-9.

Wright, P. F., and Webster, R. G. 2001. Orthomyxoviruses. 1533-79 In: Fields Virology, eds. D. M. Knipe and P. M. Howley, Lippincott Williams & Wilkins, Philadelphia.

Yoneyama, M., Kikuchi, M., Natsukawa, T., Shinobu, N., Imaizumi, T., Miyagishi, M., Taira, K., Akira, S., and Fujita, T. 2004. The RNA helicase RIG-I has an essential function in double-stranded RNA-induced innate antiviral responses. *Nat Immunol* 5: 730-7.

---

What is claimed is:

1. A method of identifying an inhibitor of influenza A virus comprising:
   preparing a reaction system comprising at least a CPSF30-binding portion of NS1A of an influenza A virus, at least a NS1A-binding portion of human CPSF30, and a candidate compound; and
   detecting binding between the at least a portion of NS1A and at least a portion of human CPSF30, wherein reduced binding in the presence of the candidate drug relative to the control is indicative of activity of the compound against influenza A virus.

2. The method of claim 1, wherein the NS1A comprises any CPSF30-binding fragments of NS1A, fragments of NS1A listed in Table 2, or the full length NS1A.

3. The method of claim 1, wherein the influenza A virus is selected from the group consisting of a human influenza A virus, a bovine influenza A virus, an equine influenza A virus, a porcine influenza A virus, an avian influenza A virus, and an avian H5N1 viral strain.

4. The method of claim 1, wherein the CPSF30 comprises a full length CPSF30, a F2F3 fragment, an F3 zinc finger, an F2F3-F2F3 tandem duplex, an F1F2F3 fragment, any soluble fragment of CPSF30, or combinations thereof.

5. The method of claim 1, wherein detecting the binding comprises a high throughput screening assay, X-ray crystallography, nuclear magnetic resonance spectroscopy, or combinations thereof.

6. The method of claim 1, wherein the detection comprises fluorescence resonance energy transfer, fluorescence polarization, immunofluorescence, chemiluminescence, radioimmunoassays, enzyme linked immunosorbent assays, mass spectrometry, luminescent bead-based proximity assay or combinations thereof.

7. The method of claim 6, wherein detection by fluorescence polarization comprises either a fluorescent labeled CPSF30 or NS1A-binding fragment thereof, a fluorescent labeled NS1A protein, or CPSF30-binding fragments thereof.

8. A process for using three-dimensional (3D) information of the CPSF30 binding site on the influenza A virus NS1A protein for designing or identifying inhibitors of an influenza A virus comprising:
   obtaining atomic coordinates for the molecular structure of at least a CPSF30-binding portion of an influenza NS1A protein, at least a NS1A-binding portion of a CPSF30 protein or both, determined either separately or as a complex; and
   designing a molecule that will fit between the influenza NS1A protein and the CPSF30 protein based on the atomic coordinates.

9. The process of claim 8, further comprising the step of using NMR spectra of at least a portion of the NS1A protein, at least a portion of the CPSF30 protein, or both, either separately or as a complex.

10. The process of claim 8, wherein the NS1A (85-215) fragment and the F2F3 fragment form a tetrameric complex.

11. The process of claim 8, wherein the atomic coordinates are obtained using X-ray crystallography.

12. The process of claim 8, further comprising the step of identifying the atoms of NS1A that constitute the CPSF30 binding portion of the NS1A protein.

13. The process of claim 8, further comprising the step of identifying the atoms of CPSF30 that constitute the NS1A binding portion of the CPSF30 protein.

14. The process of claim 8, further comprising the step of identifying the atoms of NS1A that constitute the tetramer interface of the complex formed upon binding at least a NS1A-binding portion of CPSF30 or CPSF30.

15. The process of claim 8, further comprising the step of using the expressed soluble CPSF30-binding fragments of NS1A listed in Tables 3 and 4 or NS1A.

16. The process of claim 8, further comprising the step of using crystals of the complex between NS1(85-215) and the CPSF30 F2F3 fragment.

17. A method of designing or identifying an inhibitor compound of an influenza A virus based on computational methods, comprising:
using one or more atomic coordinates of a three-dimensional structure of NS1A of an influenza A virus, a CPSF30 protein, CPSF30-binding fragments of NS1A, NS1A-binding fragments of a CPSF30 protein, or combinations thereof, determined either separately or as a complex; and
designing a molecule that will fit between the influenza NS1A protein of an influenza A virus and the CPSF30 protein based on the atomic coordinates.

18. The method of claim 17, wherein the NS1A (85-215) fragment and the F2F3 fragment form a tetrameric complex.

19. The method of claim 17, further comprising the step of using NMR spectra of at least a CPSF30-binding portion of the NS1A protein, at least a NS1A-binding portion of the CPSF30 protein, or both, either separately or as a complex.

20. The method of claim 17, in which the design is facilitated using NMR spectra of samples of NS1A(85-215) or variants thereof.

21. The method of claim 17, further comprising the step of optimizing the design of the molecule that fits between the NS1A protein and the CPSF30 protein using X-ray crystallography, NMR, synthetic chemistry and combinations thereof.

22. The method of claim 17, comprising utilizing the 3D structure of the F2F3 fragment of CPSF30, or any variant in its conformation bound to NS1A to rationally design one or more small molecule inhibitors.

23. The method of claim 17, comprising utilizing the 3D structure of the aromatic rings of the F2F3 fragment of CPSF30, or any variant in its conformation bound to NS1A to rationally design one or more small molecule inhibitors.

24. The method of claim 17, comprising the step of using the 3D structure of the F2F3 fragment of CPSF30, or any substructure, to identify one or more small molecule inhibitors by virtual screening.

25. The method of claim 17, comprising using the 3D structure of aromatic rings at the corresponding positions for Y97, F98, and F102, the corresponding positions for a sidechain at residue K101, and combinations thereof to rationally design one or more small molecule inhibitors.

26. The method of claim 17, comprising using the 3D structure of the F2F3 binding pocket in the 3D structure of NS1A bound to CPSF30 to identify one or more small molecule inhibitors by rational design.

27. The method of claim 17, comprising using the 3D structure of the F2F3 binding pocket in the 3D structure of NS1A bound to CPSF30 to identify one or more small molecule inhibitors by virtual screening.

28. The method of claim 17, using any CPSF30-binding fragments of NS1A or full length NS1A, NS1A-binding fragments of CPSF30, full length CPSF30, or combinations thereof.

29. The method of claim 17, further comprising the step of using the expressed soluble CPSF30-binding fragments of NS1A listed in Tables 3 and 4 or NS1A.

* * * * *

UNITED STATES PATENT AND TRADEMARK OFFICE
CERTIFICATE OF CORRECTION

| | | |
|---|---|---|
| PATENT NO. | : 7,709,190 B2 | Page 1 of 1 |
| APPLICATION NO. | : 11/566216 | |
| DATED | : May 4, 2010 | |
| INVENTOR(S) | : Gaetano Montelione et al. | |

It is certified that error appears in the above-identified patent and that said Letters Patent is hereby corrected as shown below:

In the Specification

Col. 1, line 16
Replace "This invention was made with U.S. Government support with under Contract Nos. AI-11772 awarded by the NIH. The government has certain rights in this invention." with
-- This invention was made with government support under Grant nos. AI011772 and GM074958 awarded by the National Institutes of Health. The government has certain rights in the invention. --

Signed and Sealed this
Sixteenth Day of June, 2015

Michelle K. Lee
*Director of the United States Patent and Trademark Office*

SEQUENCE LISTING

```
<160> NUMBER OF SEQ ID NOS: 13

<210> SEQ ID NO 1
<211> LENGTH: 230
<212> TYPE: PRT
<213> ORGANISM: Influenza A virus

<400> SEQUENCE: 1

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230

<210> SEQ ID NO 2
<211> LENGTH: 62
<212> TYPE: PRT
<213> ORGANISM: artificial
<220> FEATURE:
<223> OTHER INFORMATION: Synthetic peptide F2F3 sequence

<400> SEQUENCE: 2

Met Ser Gly Glu Lys Thr Val Val Cys Lys His Trp Leu Arg Gly Leu
```

-continued

```
                  1               5                  10                  15
Cys Lys Lys Gly Asp Gln Cys Glu Phe Leu His Glu Tyr Asp Met Thr
                     20                  25                  30

Lys Met Pro Glu Cys Tyr Phe Tyr Ser Lys Phe Gly Glu Cys Ser Asn
            35                  40                  45

Lys Glu Cys Pro Phe Leu His Ile Asp Pro Glu Ser Lys Ile
     50                  55                  60

<210> SEQ ID NO 3
<211> LENGTH: 11
<212> TYPE: PRT
<213> ORGANISM: artificial
<220> FEATURE:
<223> OTHER INFORMATION: peptide linker (GS)5G

<400> SEQUENCE: 3

Gly Ser Gly Ser Gly Ser Gly Ser Gly Ser Gly
1               5                  10

<210> SEQ ID NO 4
<211> LENGTH: 13
<212> TYPE: PRT
<213> ORGANISM: artificial
<220> FEATURE:
<223> OTHER INFORMATION: synthetic peptide (GS)6G

<400> SEQUENCE: 4

Gly Ser Gly Ser Gly Ser Gly Ser Gly Ser Gly Ser Gly
1               5                  10

<210> SEQ ID NO 5
<211> LENGTH: 56
<212> TYPE: PRT
<213> ORGANISM: artificial
<220> FEATURE:
<223> OTHER INFORMATION: synthetic peptide, Single F3-linker-F3
      construct

<400> SEQUENCE: 5

Thr Lys Met Pro Glu Cys Tyr Phe Tyr Ser Lys Phe Gly Glu Cys Ser
1               5                  10                  15

Asn Lys Glu Cys Pro Phe Leu His Ile Asp Gly Ser Asn Gly Thr Lys
            20                  25                  30

Met Pro Glu Cys Tyr Phe Tyr Ser Lys Phe Gly Glu Cys Ser Asn Lys
        35                  40                  45

Glu Cys Pro Phe Leu His Ile Asp
    50                  55

<210> SEQ ID NO 6
<211> LENGTH: 87
<212> TYPE: PRT
<213> ORGANISM: artificial
<220> FEATURE:
<223> OTHER INFORMATION: synthetic peptide F2F3-F3

<400> SEQUENCE: 6

Met Ser Gly Glu Lys Thr Val Val Cys Lys His Trp Leu Arg Gly Leu
1               5                  10                  15

Cys Lys Lys Gly Asp Gln Cys Glu Phe Leu His Glu Tyr Asp Met Thr
            20                  25                  30

Lys Met Pro Glu Cys Tyr Phe Tyr Ser Lys Phe Gly Glu Cys Ser Asn
        35                  40                  45
```

Lys Glu Cys Pro Phe Leu His Ile Asp Gly Ser Asn Gly Thr Lys Met
 50                  55                  60

Pro Glu Cys Tyr Phe Tyr Ser Lys Phe Gly Glu Cys Ser Asn Lys Glu
 65                  70                  75                  80

Cys Pro Phe Leu His Ile Asp
                 85

<210> SEQ ID NO 7
<211> LENGTH: 15
<212> TYPE: PRT
<213> ORGANISM: artificial
<220> FEATURE:
<223> OTHER INFORMATION: synthetic peptide linker (GS)7G

<400> SEQUENCE: 7

Gly Ser Gly Ser Gly Ser Gly Ser Gly Ser Gly Ser Gly Ser Gly
 1               5                  10                  15

<210> SEQ ID NO 8
<211> LENGTH: 17
<212> TYPE: PRT
<213> ORGANISM: artificial
<220> FEATURE:
<223> OTHER INFORMATION: synthetic peptide linker

<400> SEQUENCE: 8

Gly Ser Gly Ser Gly Ser Gly Ser Gly Ser Gly Ser Gly Ser Gly Ser
 1               5                  10                  15

Gly

<210> SEQ ID NO 9
<211> LENGTH: 116
<212> TYPE: PRT
<213> ORGANISM: artificial
<220> FEATURE:
<223> OTHER INFORMATION: synthetic peptide F2F3 linker F2F3

<400> SEQUENCE: 9

Met Ser Gly Glu Lys Thr Val Val Cys Lys His Trp Leu Arg Gly Leu
 1               5                  10                  15

Cys Lys Lys Gly Asp Gln Cys Glu Phe Leu His Glu Tyr Asp Met Thr
             20                  25                  30

Lys Met Pro Glu Cys Tyr Phe Tyr Ser Lys Phe Gly Glu Cys Ser Asn
         35                  40                  45

Lys Glu Cys Pro Phe Leu His Ile Asp Gly Ser Asn Gly Gly Glu Lys
 50                  55                  60

Thr Val Val Cys Lys His Trp Leu Arg Gly Leu Cys Lys Lys Gly Asp
 65                  70                  75                  80

Gln Cys Glu Phe Leu His Glu Tyr Asp Met Thr Lys Met Pro Glu Cys
             85                  90                  95

Tyr Phe Tyr Ser Lys Phe Gly Glu Cys Ser Asn Lys Glu Cys Pro Phe
            100                 105                 110

Leu His Ile Asp
        115

<210> SEQ ID NO 10
<211> LENGTH: 85
<212> TYPE: PRT
<213> ORGANISM: artificial
<220> FEATURE:
<223> OTHER INFORMATION: synthetic peptide F3-F2F3

-continued

```
<400> SEQUENCE: 10

Thr Lys Met Pro Glu Cys Tyr Phe Tyr Ser Lys Phe Gly Glu Cys Ser
1               5                   10                  15

Asn Lys Glu Cys Pro Phe Leu His Ile Asp Gly Ser Asn Gly Gly Glu
            20                  25                  30

Lys Thr Val Val Cys Lys His Trp Leu Arg Gly Leu Cys Lys Lys Gly
        35                  40                  45

Asp Gln Cys Glu Phe Leu His Glu Tyr Asp Met Thr Lys Met Pro Glu
    50                  55                  60

Cys Tyr Phe Tyr Ser Lys Phe Gly Glu Cys Ser Asn Lys Glu Cys Pro
65                  70                  75                  80

Phe Leu His Ile Asp
            85

<210> SEQ ID NO 11
<211> LENGTH: 63
<212> TYPE: PRT
<213> ORGANISM: artificial
<220> FEATURE:
<223> OTHER INFORMATION: synthetic peptide Leu Arg linker

<400> SEQUENCE: 11

Leu Arg Gly Ser Gly Ser Gly Thr Lys Met Pro Glu Cys Tyr Phe Tyr
1               5                   10                  15

Ser Lys Phe Gly Glu Cys Ser Asn Lys Glu Cys Pro Phe Leu His Ile
            20                  25                  30

Asp Gly Ser Asn Gly Thr Lys Met Pro Glu Cys Tyr Phe Tyr Ser Lys
        35                  40                  45

Phe Gly Glu Cys Ser Asn Lys Glu Cys Pro Phe Leu His Ile Asp
    50                  55                  60

<210> SEQ ID NO 12
<211> LENGTH: 63
<212> TYPE: PRT
<213> ORGANISM: artificial
<220> FEATURE:
<223> OTHER INFORMATION: synthetic peptide Arg Leu linker

<400> SEQUENCE: 12

Arg Leu Gly Ser Gly Ser Gly Thr Lys Met Pro Glu Cys Tyr Phe Tyr
1               5                   10                  15

Ser Lys Phe Gly Glu Cys Ser Asn Lys Glu Cys Pro Phe Leu His Ile
            20                  25                  30

Asp Gly Ser Asn Gly Thr Lys Met Pro Glu Cys Tyr Phe Tyr Ser Lys
        35                  40                  45

Phe Gly Glu Cys Ser Asn Lys Glu Cys Pro Phe Leu His Ile Asp
    50                  55                  60

<210> SEQ ID NO 13
<211> LENGTH: 269
<212> TYPE: PRT
<213> ORGANISM: influenza A

<400> SEQUENCE: 13

Met Gln Glu Ile Ile Ala Ser Val Asp His Ile Lys Phe Asp Leu Glu
1               5                   10                  15

Ile Ala Val Glu Gln Gln Leu Gly Ala Gln Pro Leu Pro Phe Pro Gly
            20                  25                  30

Met Asp Lys Ser Gly Ala Ala Val Cys Glu Phe Phe Leu Lys Ala Ala
```

-continued

```
                35                  40                  45
Cys Gly Lys Gly Gly Met Cys Pro Phe Arg His Ile Ser Gly Glu Lys
 50                      55                      60
Thr Val Val Cys Lys His Trp Leu Arg Gly Leu Cys Lys Lys Gly Asp
 65                  70                  75                  80
Gln Cys Glu Phe Leu His Glu Tyr Asp Met Thr Lys Met Pro Glu Cys
                 85                  90                  95
Tyr Phe Tyr Ser Lys Phe Gly Glu Cys Ser Asn Lys Glu Cys Pro Phe
             100                 105                 110
Leu His Ile Asp Pro Glu Ser Lys Ile Lys Asp Cys Pro Trp Tyr Asp
         115                 120                 125
Arg Gly Phe Cys Lys His Gly Pro Leu Cys Arg His Arg His Thr Arg
     130                 135                 140
Arg Val Ile Cys Val Asn Tyr Leu Val Gly Phe Cys Pro Glu Gly Pro
145                 150                 155                 160
Ser Cys Lys Phe Met His Pro Arg Phe Glu Leu Pro Met Gly Thr Thr
                165                 170                 175
Glu Gln Pro Pro Leu Pro Gln Gln Thr Gln Pro Pro Ala Lys Gln Ser
            180                 185                 190
Asn Asn Pro Pro Leu Gln Arg Ser Ser Ser Leu Ile Gln Leu Thr Ser
            195                 200                 205
Gln Asn Ser Ser Pro Asn Gln Gln Arg Thr Pro Gln Val Ile Gly Val
    210                 215                 220
Met Gln Ser Gln Asn Ser Ser Ala Gly Asn Arg Gly Pro Arg Pro Leu
225                 230                 235                 240
Glu Gln Val Thr Cys Tyr Lys Cys Gly Glu Lys Gly His Tyr Ala Asn
            245                 250                 255
Arg Cys Thr Lys Gly His Leu Ala Phe Leu Ser Gly Gln
            260                 265
```